(12) United States Patent
Roberts et al.

(10) Patent No.: US 12,161,619 B2
(45) Date of Patent: Dec. 10, 2024

(54) COMPOSITIONS AND METHOD FOR TREATING AND PREVENTING MALNUTRITION

(71) Applicant: TUFTS UNIVERSITY, Medford, MA (US)

(72) Inventors: Susan Roberts, Medford, MA (US); Amy Ernst, Medford, MA (US); Edward Saltzman, Medford, MA (US)

(73) Assignee: TRUSTEES OF TUFTS COLLEGE, Medford, MA (US)

( * ) Notice: Subject to any disclaimer, the term of this patent is extended or adjusted under 35 U.S.C. 154(b) by 66 days.

(21) Appl. No.: 17/475,513

(22) Filed: Sep. 15, 2021

(65) Prior Publication Data

US 2022/0000836 A1    Jan. 6, 2022

Related U.S. Application Data

(63) Continuation of application No. 16/068,529, filed as application No. PCT/US2016/067779 on Dec. 20, 2016, now Pat. No. 11,135,195.

(60) Provisional application No. 62/276,347, filed on Jan. 8, 2016.

(51) Int. Cl.

| | | |
|---|---|---|
| A61K 36/00 | (2006.01) | |
| A61K 9/00 | (2006.01) | |
| A61K 31/202 | (2006.01) | |
| A61K 31/353 | (2006.01) | |
| A61K 31/522 | (2006.01) | |
| A61K 36/16 | (2006.01) | |
| A61K 36/185 | (2006.01) | |
| A61K 36/21 | (2006.01) | |
| A61K 36/45 | (2006.01) | |
| A61K 36/48 | (2006.01) | |
| A61K 36/53 | (2006.01) | |
| A61K 36/537 | (2006.01) | |
| A61K 36/54 | (2006.01) | |
| A61K 36/55 | (2006.01) | |
| A61K 36/81 | (2006.01) | |
| A61K 36/82 | (2006.01) | |
| A61K 36/8962 | (2006.01) | |
| A61K 36/9066 | (2006.01) | |
| A61K 45/06 | (2006.01) | |

(52) U.S. Cl.
CPC .......... *A61K 31/353* (2013.01); *A61K 9/0056* (2013.01); *A61K 31/202* (2013.01); *A61K 31/522* (2013.01); *A61K 36/16* (2013.01); *A61K 36/185* (2013.01); *A61K 36/21* (2013.01); *A61K 36/45* (2013.01); *A61K 36/48* (2013.01); *A61K 36/53* (2013.01); *A61K 36/537* (2013.01); *A61K 36/54* (2013.01); *A61K 36/55* (2013.01); *A61K 36/81* (2013.01); *A61K 36/82* (2013.01); *A61K 36/8962* (2013.01); *A61K 36/9066* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 8,053,007 B2 | 11/2011 | Innocenzi | |
| 8,088,431 B2 | 1/2012 | Ward et al. | |
| 8,221,804 B2 | 7/2012 | Stock et al. | |
| 8,282,976 B2 | 10/2012 | Dörr et al. | |
| 8,367,121 B2 | 2/2013 | Mazzio et al. | |
| 2010/0159105 A1 | 6/2010 | Zhu | |
| 2010/0215781 A1* | 8/2010 | Opheim | A61K 31/05 424/729 |
| 2011/0293790 A1* | 12/2011 | Ewing | A23L 33/10 426/648 |
| 2013/0156872 A1 | 6/2013 | Giuliano et al. | |
| 2014/0045932 A1 | 2/2014 | Sies | |
| 2014/0080791 A1 | 3/2014 | Berge et al. | |
| 2015/0004282 A1* | 1/2015 | Mills | A23L 33/15 426/72 |
| 2015/0017147 A1 | 1/2015 | Gillespie | |

FOREIGN PATENT DOCUMENTS

| | | |
|---|---|---|
| WO | WO 2012/113771 | 8/2012 |
| WO | WO 2013/106371 | 7/2013 |

OTHER PUBLICATIONS

Abbaspour N. et al. "Review on iron and its importance for human health." Journal of research in medical sciences : the official journal of Isfahan University of Medical Sciences. 2014; 19(2):164-74.
Ansari et al. (2012) Food and Public Health, 2(6): 241-253.
Batra et al. "A Randomized Controlled Trial Offering Higher-Compared with Lower-Dairy Second Meals Daily in Preschools in Guinea-Bissau Demonstrates an Attendance-Dependent Increase in Weight Gain for Both Meal Types and an Increase in Mid-Upper Arm Circumference for the Higher-Dairy Meal." J Nutr. Jan. 2016; 146(1):124-32.
Bogale A, et al. "Nutritional status and cognitive performance of mother-child pairs in Sidama, Southern Ethiopia." Maternal & child nutrition. 2013;9(2):274-84. Epub Aug. 3, 2011.
Calder PC. Omega-3 fatty acids and inflammatory processes. Nutrients. 2010;2(3):355-74.
Carlson et al. "Executive function and theory of mind: stability and prediction from ages 2 to 3." Dev Psychol. Nov. 2004;40(6):1105-22.
Da Costa et al. "Choline deficiency in mice and humans is associated with increased plasma homocysteine concentration after a methionine load." The American journal of clinical nutrition. 2005;81(2):440-4.
Ermakov IV, et al. Noninvasive selective detection of lycopene and β-carotene in human skin using Raman spectroscopy. BIOMEDO. 2004;9(2):332-8.

(Continued)

*Primary Examiner* — Russell G Fiebig
(74) *Attorney, Agent, or Firm* — Casimir Jones, S.C.; Tanya A. Arenson

(57) ABSTRACT

Provided herein are compositions and methods for treating, preventing, and reversing malnutrition. In particular, provided herein are compositions and methods for facilitating cognitive repair and preventing obesity (e.g. in children).

13 Claims, 1 Drawing Sheet

(56) References Cited

OTHER PUBLICATIONS

=Ferland, G. "Vitamin K and the nervous system: an overview of its actions." Adv. Nutr. Bethesda, Md. 2012;3(2):204-12.
Fieige et al. (2010) Nutrition Reviews, vol. 68(5): 290-315.
Grantham-McGregor S, and Ani C. A review of studies on the effect of iron deficiency on cognitive development in children. The Journal of nutrition. 2001;131(2s-2):649S-66S; discussion 66S-68S.
Hata TR, Scholz TA, Ermakov IV, McClane RW, Khachik F, Gellermann W, Pershing LK. Non-invasive raman spectroscopic detection of carotenoids in human skin. The Journal of investigative dermatology. 2000;115(3):441-8. Epub.
Hsu DP, French AJ, Madson SL, Palmer JM, Gidvani-Diaz V. Evaluation of a Noninvasive Hemoglobin Measurement Device to Screen for Anemia in Infancy. Maternal and child health journal. 2016;20(4):827-32. Epub.
Husaini MA, Karyadi L, Husaini YK, Sandjaja, Karyadi D, Pollitt E. developmental effects of short-term supplementary feeding in nutritionally-at-risk Indonesian infants. The American journal of clinical nutrition. 1991;54(5):799-804.
Kuratko CN, et al. The relationship of docosahexaenoic acid (DHA) with learning and behavior in healthy children: a review. Nutrients. 2013;5(7):2777-810.
Lin et al. "Non-invasive Optical Measurement of Cerebral Metabolism and Hemodynamics in Infants" 2013, J Vis Exp 2013; E4379, 9 pages.
Mendez MA, Adair LS. Severity and timing of stunting in the first two years of life affect performance on cognitive tests in late childhood. The Journal of nutrition. 1999; 129(8):1555-62.
Nahar B, et al. Effects of a community-based approach of food and psychosocial stimulation on growth and development of severely malnourished children in Bangladesh: a randomized trial. European journal of clinical nutrition. 2012;66(6):701-9.
Nehlig, A. "The neuroprotective effects of cocoa flavanol and its influence on cognitive performance" Br J Clin Pharmacol. Mar. 2013;75(3):716-27.
Noriega et al. (2014) Nutrients 6; 3516-3535.
Perez-Exposito et al. (2009) Nutrition Reviews vol. 67(12): 706-718.
Pollitt E, et al. Three-month nutritional supplementation in Indonesian infants and toddlers benefits memory function 8 y later. The American journal of clinical nutrition. 1997;66(6):1357-63.
Prado EL, Dewey KG. Nutrition and brain development in early life. Nutrition reviews. 2014;72(4):267-84.
Sudfeld et al. Malnutrition and Its Determinants Are Associated with Suboptimal Cognitive, Communication, and Motor Development in Tanzanian Children. The Journal of nutrition. 2015;145(12):2705-14.
The Global Effort to Reduce Child Hunger and Increase School Attendance Report to the United States Congress, Fiscal Years 2012-2014. 2016 Jun. 2016. Report No. 16. Specialized nutritious foods, (2016).
Webb et al. Apr. 2011, Delivering Improved Nutrition: Recommendations for Changes to U.S. Food Aid Products and Programs. Boston, MA: Tufts University, 56 pages.
Weschler 1989, Wechsler Preschool and Primary Scale of Intelligence—Revised. San Antonio, TX: The Psychological Corporation, 19 pages.
Zeisel SH, da Costa KA. Choline: an essential nutrient for public health. Nutrition reviews. 2009;67(11):615-23.

\* cited by examiner

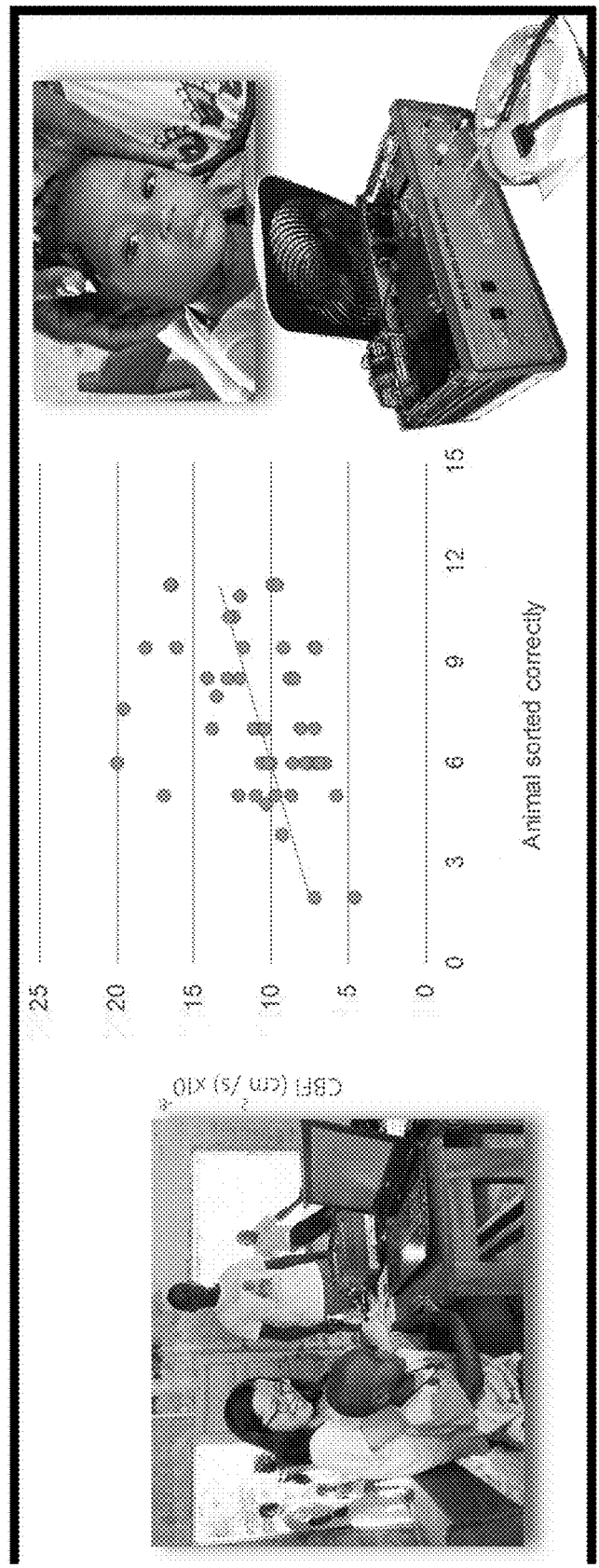

COMPOSITIONS AND METHOD FOR TREATING AND PREVENTING MALNUTRITION

This application is a continuation of U.S. patent application Ser. No. 16/068,529, filed Jul. 6, 2018, which is a National Stage Application of PCT/US2016/067779, filed Dec. 20, 2016, and claims priority to Provisional Patent Application Ser. No. 62/276,347, filed Jan. 8, 2016, which are herein incorporated by reference in their entirety.

FIELD

Provided herein are compositions and methods for treating, preventing, and reversing malnutrition. In particular, provided herein are compositions and methods for facilitating cognitive repair and preventing current or future obesity (e.g. in children or the elderly) while simultaneously preventing or treating malnutrition.

BACKGROUND

Individuals who are malnourished early in life suffer from long-term negative effects. This is true both for severe acute malnutrition (SAM) and moderate acute malnutrition (MAM), as well as lesser forms of undernutrition that cause stunting, anemia, poor growth and moderate but not immediately life-threatening micronutrient deficiencies. The problems that individuals who are malnourished early in life suffer from, if they survive childhood, frequently include cognitive impairment, stunting, and increased susceptibility to obesity. Obesity, in turn, reduces productive lifespan, increases the risk of debilitating chronic diseases such as diabetes, cardiometabolic disorders, stroke and cancers, and also reduces the likelihood that individuals are able to lead healthy, productive lives. Furthermore, because malnutrition can begin in utero, the same considerations of nutrition to prevent malnutrition apply to pregnant mothers.

According to UNICEF (2014) there are 51 million children under five years old who suffer from acute malnutrition annually, and another 160 million who have lesser forms of malnutrition that impair developmental potential and cause stunting. For these reasons, demand for ready-to-use and other supplementary foods to prevent or treat malnutrition has grown rapidly, but current supply addresses only 2.6 million cases per year.

Malnutrition in disadvantaged children in affluent countries such as the U.S is not widely recognized, but malnutrition is not restricted to developing countries, and also occurs in children eating diets of low nutritional quality worldwide. This is true even in infants and children who are obese, but are malnourished due to the low nutritional quality of consumed foods.

In the past, the problems that malnourished children suffer from later in life have been attributed to the long-term effects of the malnutrition itself, rather than the current methods and products designed to treat and prevent malnutrition. Thus, the goal of current products to feed children with malnutrition or at risk of malnutrition is merely to "re-nourish" them, i.e. to return them to a state where so-called essential micronutrients in the body are in the adequate ranges. However, merely re-nourishing with the essential nutrients does not address the problem that brain and bodily tissues have been damaged and will stay damaged unless actively repaired. Currently, no malnutrition formulations appear to do this. Furthermore, since some of the current malnutrition food products are missing nutrients that are needed for maintenance of brain and bodily functions, they actually increase the cognitive and bodily problems of post-malnourished children. Examples of bodily problems include increased susceptibility to obesity via their entraining preference for very sweet foods that promote overeating, and also increase inflammation and reduce gains of lean tissue relative to fat tissue.

Current food product formulations to prevent or treat malnutrition fall into two distinct categories, each with a fundamental similarity in the principles of their formulation:

Lipid-rich shelf-stable ready-to-use formulations with characteristically low water content that have a range of uses (e.g. consumed as the entire or partial diet, or a mix added as an enrichment to home-prepared foods): Examples including the Plump'-y-nut range of products and the lipid-rich ready-to-use products produced for UNICEF by various manufacturers.

Mixes and powders that are not high in lipids and are not ready-to-use, which can be made up into gruels, liquids etc. via adding a fluid such as water, or added as an enrichment to home-prepared foods. Examples included the fortified corn-soy blends that are core products of USAID.

Both these types of products have the same conceptual basis, which is that they have a low water content for shelf stability and the macronutrients (fat, protein and carbohydrate) are derived from mixtures of inexpensive commodities of low nutritional value such as sugar, corn flour and soy flour, with minimal amounts of higher-cost ingredients to provide fat and protein (e.g. peanuts and milk powder). On top of that micronutrients are added as purified preparations rather than coming from nutrient-dense ingredients.

However, a substantial problem with this traditional approach is that existing products are lacking food constituents that can facilitate repair and recovery in relation to malnutrition with respect to long-term health and cognition.

Additional compositions and methods for treating malnourishment are needed.

DESCRIPTION OF THE DRAWING

FIG. 1 shows the relationship between brain blood flow, cognition, and head circumference.

SUMMARY

Provided herein are compositions and methods for a new class of products for treating, preventing, and reversing malnutrition. In particular, provided herein are compositions and methods for facilitating cognitive repair and preventing later obesity (e.g. in children). In addition, some formulations can prevent or reverse age-associated cognitive decline in elderly individuals whether they are malnourished or not. In some embodiments, the present disclosure provides compositions including one or more of the following in products to prevent and or treatment of malnutrition (in addition to generally recognized constituents such as calories and essential nutrients), none of which are currently included or used for this purpose in children: food ingredients that contain flavonoids that cross the blood brain barrier, the omega-3 fatty acids such as DHA/EPA that are needed for brain repair, and caffeine; also use of purified versions of these three chemical categories for the same purpose of preventing and or treating malnutrition.

For example, in some embodiments, the present disclosure provides a composition, comprising, consisting essentially of, or consisting of a) at least 20 mg/day (e.g. at least 50, at least 100, or more) of a plurality of flavonoids (e.g., flavonoids that cross the blood-brain barrier), wherein at least one of said flavonoids is catechin or epicatechin; b) at least 0.1 g/day (e.g., at least 0.1, 0.5, 0.6, 0.7, 0.8, 0.9, or 1.0 g/day) of omega-3 fatty acids, wherein said omega-3 fatty acids comprise EPA and DHA; and c) at least 1 mg/day caffeine. In some embodiments, the daily dose is provided in one or more compositions. In some embodiments, the composition comprises 20-2000 mg of flavonoids. In some embodiments, the composition comprises at least 300-500 mg of flavonoids. In some embodiments, the composition comprises 200-500 mg of catechin and/or epicatechin or other flavanols. In some embodiments, the catechin and/or epicatechin are in cocoa, and/or green tea or tea extracts. In some embodiments, the flavonoids are one or more additional flavonoids selected from, for example, cocoa, tea (e.g., green or black), tea extracts, quercetin, kaempferol, tomato, acai berry, green vegetables (e.g., kale or spinach), moringa, blueberry, gingko balboa, onion, cherry tomato, cinnamon, flax seeds, chia sees, legumes, or curcumin. In some embodiments, the composition comprises at least 50 mg (e.g., 50-1800 mg) of the additional flavonoids. In some embodiments, the composition comprises at least 150 mg (e.g., 200-1500 or 200-500 mg) of DHA. In some embodiments, the EPA and/or DHA is in fish oil. In some embodiments, the composition comprises 1-5 mg/kg per day body weight caffeine or 1-50 mg caffeine. In some embodiments, the caffeine is found in said cocoa and/or green tea or green tea extracts or purified caffeine. In some embodiments, the composition further comprises a plurality of micronutrients. In some embodiments, the micronutrients are vitamins and/or minerals (e.g., one or more of iron, phosphorous, zinc, thiamine, riboflavin, niacin, vitamin B6, folate, vitamin, B12, pantothenic acid, biotin, choline, chromium, copper, manganese, selenium molybdenum, iodine, vitamin A, calcium, potassium, magnesium, vitamin E, vitamin C, a carotenoid, vitamin D, or vitamin K). In some embodiments, added iron is eliminated from formulations designed for elderly adults.

The present disclosure is not limited to particular formulations. Additional formulations are specifically contemplated. For example, in some embodiments, the composition comprises cashews or peanuts, sugar or honey, vegetable oil, raw eggs, a protein mix, high-flavanol cocoa, cinnamon, moringa powder, tomato powder, green tea powder, vitamin powder, and fish oil fortified with fat soluble vitamins or extracts or fractions thereof (e.g., 18 g cashews, 3 g sugar or honey, 3.25 g vegetable oil, 4 g eggs, 10 g protein mix comprising 4 g whey protein and 6 g soy protein isolate, 5.0 g high-flavanol cocoa, 0.5 cinnamon, 1 g moringa powder, 1.5 g tomato powder, 3.0 g green tea powder, 0.15 g vitamin/mineral powder, and 1.7 ml fish oil fortified with fat soluble vitamins per serving).

In some embodiments, the composition comprises cashew butter, sorghum flour, vegetable oil, whole eggs, spinach powder, onion powder, moringa powder, tomato powder, green tea powder, turmeric, protein mix, vitamin powder, and fish oil fortified with fat soluble vitamins or extracts or fractions thereof (e.g., 20.6 g cashew butter, 6.5 g sorghum flour, 3 g vegetable oil, 1 g whole eggs, 2.8 g spinach powder, 0.2 g onion powder, 1.4 g moringa powder, 1 g tomato powder, 3.7 g green tea powder, 0.2 g turmeric, 21 g protein mix comprising 16 g canned salmon and 5 g soy protein isolate, 0.1 g vitamin powder, and 1.7 ml fish oil fortified with fat soluble vitamins per serving).

In some embodiments, the composition comprises cashew butter, sorghum flour, honey, soybean oil, salt, cocoa powder, spinach powder, onion powder, moringa powder, tomato powder, green tea powder, turmeric, protein mix, vitamin powder, and fish oil fortified with fat soluble vitamins or extracts or fractions thereof (e.g., 20.6 g cashew butter, 7 g sorghum flour, 4.8 g honey, 3.5 g soybean oil, 0.3 g salt, 4.0 g cocoa powder, 3.0 g spinach powder, 0.2 g onion powder, 1.5 g moringa powder, 1 g tomato powder, 4.0 g green tea powder, 0.2 g turmeric, 20 g protein mix comprising 13 g canned salmon, 1 g egg, and 6 g soy protein isolate, 0.1 g vitamin powder, and 1.7 ml fish oil fortified with fat soluble vitamins per serving).

In some embodiments, the composition comprises cocoa powder, spinach powder, onion powder, moringa powder, tomato powder, green tea powder, turmeric, salmon powder, soy protein isolate, vitamin powder, and fish oil fortified with fat soluble vitamins or extracts or fractions thereof (e.g., 4.0 g cocoa powder, 3.0 g spinach powder, 0.2 g onion powder, 1.5 g moringa powder, 1 g tomato powder, 4.0 g green tea powder, 0.2 g turmeric, 3 g powdered salmon, 6 g soy protein isolate, 0.1 g vitamin powder, and 1.7 ml fish oil fortified with fat soluble vitamins per serving).

In some embodiments, the composition comprises cocoa powder, spinach powder, onion powder, moringa powder, tomato powder, green tea powder, turmeric, vitamin powder, and fish oil fortified with fat soluble vitamins or extracts or fractions thereof (e.g., 4.0 g cocoa powder, 3.0 g spinach powder, 0.2 g onion powder, 1.5 g moringa powder, 1 g tomato powder, 4.0 g green tea powder, 0.2 g turmeric, 0.1 g vitamin powder, and 1.7 ml fish oil fortified with fat soluble vitamins per serving). In some embodiments, composition comprises cashew butter, dextrose, soybean oil, cocoa powder, spinach powder, vitamin powder, whey, and fish oil fortified with fat soluble vitamins (e.g., 20 g cashew butter, 10 g dextrose, 4.0 g soybean oil, 4.0 g cocoa powder, 7.0 g spinach powder, 0.15 g vitamin powder, 4.5 g whey, and 1.9 ml fish oil fortified with fat soluble vitamins per serving).

In some embodiments, the composition comprises cocoa powder, spinach powder, green tea powder, vitamin powder, fish protein, soy protein, rice flour, dextrose, soybean oil, and DHA-rich oil fortified with fat soluble vitamins or extracts or fractions thereof (e.g., 4.4 g cocoa powder, 5.3 g spinach powder, 2.4 g green tea powder, 0.1 g vitamin powder, 5 g fish protein, 2 g soy protein, 10 g rice flour, 4 g dextrose, 13.4 g soybean oil, and 1.9 ml DHA-rich oil fortified with fat soluble vitamins per serving).

In some embodiments, the composition comprises cocoa powder, moringa powder, matcha powder, soy protein powder, flaxseed powder, cinnamon, salt, honey, soybutter, raisins, water, whey protein powder, omega 3 oil, chocolate chips, sprinkles, beta carotene, vitamin C, vitamin D, vitamin E, vitamin K, thiamine, riboflavin, niacin, vitamin B6, vitamin B12, pantothenic acid, biotin, choline, chromium, copper, iodine, manganese, molybdenum, selenium, and zinc and optionally iron. In some embodiments, the composition comprises 3-4 g cocoa powder, 0.1-0.5 g moringa powder, 0.1-1.0 g matcha powder, 1-10 g soy protein powder, 0.1-1.0 g flaxseed powder, 0.01-0.1 g cinnamon, 0.1-0.5 g salt, 1-5 g honey, 5-15 g soybutter, 1-10 g raisins, 5-10 ml water, 1-5 g whey protein powder, 1-3 g omega 3 oil, 1-5 g chocolate chips, sprinkles, 0.0002-0.00075 g beta carotene, 0.002-0.005 g vitamin C, 0.000001-0.000005 g vitamin D, 0.001-0.002 g vitamin E, 0.000007-0.00001 g vitamin K, 0.00005-0.0001 g thiamine, 0.00002-0.00006 g riboflavin, 0.001-0.0015 g niacin, 0.00005-0.0001 g vitamin B6, 0.0000001-0.0000002 g vitamin B12, 0.0002-0.0006 g pantothenic acid, 0.000001-0.000004 g biotin, 0.025-0.075 g choline, 0.000001-0.000005 g chromium, 0.00005-0.0001 g copper, 0.00001-0.00002 g iodine, 0.0005-0.0010 g iron, 0.0001-0.0005 g manganese, 0.000001-0.000008 g molybdenum, 0.000001-0.00001 g selenium, and 0.0001-0.0005 g zinc per serving (e.g., 3.5 g cocoa powder, 0.25 g moringa powder, 0.5 g matcha powder, 5.0 g soy protein powder, 0.5 g flaxseed powder, 0.05 g cinnamon, 0.1 g salt, 2.75 g honey, 8.5 g soybutter, 5.0 g raisins, 7.5 ml water, 2.5 g whey protein powder, 1.71 g omega 3 oil, 2.0 g chocolate chips, sprinkles, 0.00053 g beta carotene, 0.00365 g vitamin C, 0.00000375 g vitamin D, 0.00113 g vitamin E, 0.0000092 g vitamin K, 0.000082 g thiamine, 0.000041 g riboflavin, 0.00125 g niacin, 0.00009 g vitamin B6, 0.00000018 g vitamin B12, 0.00048 g pantothenic acid, 0.0000025 g biotin, 0.0501 g choline, 0.0000033 g chromium, 0.000098 g copper, 0.000018 g iodine, optionally 0.00079 g iron, 0.00036 g manganese, 0.000004 g molybdenum, 0.000005 g selenium, and 0.00030 g zinc per serving).

In some embodiments, the composition comprises cocoa powder, moringa, matcha, soy protein, whey protein, cinnamon, salt, honey, omega 3 oil, peanut butter, vegetable oil, sugar, vitamin tablet, beta carotene, vitamin C, vitamin D, vitamin E, vitamin K, niacin, vitamin B6, choline, chromium, iodine, magnesium, manganese, molybdenum, selenium, and zinc. In some embodiments, the composition comprises 6-8 g cocoa powder, 0.3-0.6 g moringa, 0.7-1.0 g matcha, 7-10 g soy protein, 4-6 g whey protein, 0.07-0.11 g cinnamon, 0.1-0.2 g salt, 7-10 g honey, 1-2 g omega 3 oil, 12-18 g peanut butter, 5-8 g vegetable oil, 3-5 g sugar, 1-1.5 g vitamin tablet, 0.0001-0.0002 g beta carotene, 0.08-0.1 g vitamin C, 0.000004-0.000005 vitamin D, 0.01-0.02 g vitamin E, $1 \times 10^{-5}$-$2 \times 10^{-6}$ g vitamin K, 0.001-0.01 g niacin, 0.0001-0.0002 g vitamin B6, 0.02-0.04 g choline, 0.00000001-0.00000003 g chromium, 0.00003-0.00004 g iodine, 0.01-0.02 g magnesium, 0.001-0.002 g manganese, 0.00002-0.00003 g molybdenum, $3.00 \times 10^{-5}$-$4.00 \times 10^{-5}$ g selenium, and 0.002-0.004 g zinc per serving (e.g., 6.08 g cocoa powder, 0.42 g moringa, 0.83 g matcha, 7.5 g soy protein, 4.3 g whey protein, 0.08 g cinnamon, 0.13 g salt, 8 g honey, 1.42 g omega 3 oil, 13.8 g peanut butter, 5.83 g vegetable oil, 3.5 g sugar, 1.14 g vitamin tablet, 0.00018 g beta carotene, 0.0937 g vitamin C, 0.0000046805 vitamin D, 0.011 g vitamin E, $1.51 \times 10^{-6}$ g vitamin K, 0.00865 g niacin, 0.000118 g vitamin B6, 0.0381 g choline, 0.000000015 g chromium, 0.000033 g iodine, 0.0176 g magnesium, 0.0015 g manganese, 0.0000225 g molybdenum, $3.85 \times 10^{-5}$ g selenium, and 0.00297 g zinc per serving or 7.3 g cocoa powder, 0.5 g moringa, 1.0 g matcha, 9.0 g soy protein, 5.2 g whey protein, 0.1 g cinnamon, 0.15 g salt, 9.5 g honey, 1.71 g omega 3 oil, 16.5 g peanut butter, 7.0 g vegetable oil, 4.2 g sugar, 1.14 g vitamin tablet, 0.0939 g vitamin C, 0.000004 g vitamin D, 0.011 g vitamin E, 0.00004 g vitamin K, 0.003 g niacin, 0.0001 g vitamin B6, 0.022 g choline, 0.00000002 g chromium, 0.000033 g iodine, 0.00153 g manganese, 0.0000225 g molybdenum, and 0.00334 g zinc per serving).

In some embodiments, the composition is a nutritional or dietary supplement.

In some embodiments, the present disclosure provided a food product that provides all or daily food or a percentage of daily food comprising any of the aforementioned compositions. In some embodiments, the food product is a food or a food additive. In some embodiments, the food is a powder, a capsule, a baked good, a raw or cooked bar, a paste, or a liquid. In some embodiments, all or part of a subjects daily food is provided in one or more of the aforementioned compositions or similar. In some embodiments, the food comprises one or more of protein, carbohydrate, or fat. In some embodiments, the food comprises at least 50 kcal (e.g., at least 50, 100, 200, or 300 kcal). In some embodiments, the food comprises approximately 11-35% of it calories from protein, 10-50% of its calories from carbohydrates, and 30-60% of its calories from fat (e.g., approximately 25% of its calories from protein, 30% of its calories from carbohydrates, and 45% of its calories from fat).

Additional embodiments provide a method or use of treating or preventing malnutrition, comprising: administering (e.g., by a caretaker, healthcare provider, or self-administration) one or more of any of the aforementioned compositions or foods to a subject in need thereof. In some embodiments, the composition or food is administered with a drink that forms part of the treatment (e.g., a drink comprising nonfat dried milk, honey or sugar, and high-flavanol cocoa powder and/or green tea (e.g., 3 g nonfat dried milk, 2.3 g honey, and 5 g high-flavanol cocoa powder per serving)). In some embodiments, the subject is an infant, pregnant woman, fetus (e.g., by administering the composition to a pregnant woman) or a child. In some embodiments, the subject is not an adult. In some embodiments, the subject has been suffering from malnutrition for at least one week (e.g., at least one week, one month, one year, etc.). In some embodiments, the subject is not suffering from a wasting disease or condition (e.g., a disease or condition unrelated to malnutrition). In some embodiments, the administering improves the cognitive function, growth, or brain activity of the subject. In some embodiments, the administering repairs or prevents cognitive damage caused by malnutrition. In some embodiments, the administering improves cognitive function to the level of a subject not suffering from malnutrition. In some embodiments, the composition or food is administered one or more times per day for a period of one day to one year or longer, including in school feeding programs for routine use during the school year as a meal or snack. In some embodiments, the composition or food is administered one or more times per day for a period of one week to 6 months. In some embodiments, the subject is not an adult. In some embodiments, the subject is not adequately nourished.

Additional embodiments are described herein.

Definitions

As used herein, the term "omega-3 fatty acid" refers to polyunsaturated fatty acids that have the final double bond in the hydrocarbon chain between the third and fourth carbon atoms from the methyl end of the molecule. Non-limiting examples of omega-3 fatty acids include, 5,8,11,14,17-eicosapentaenoic acid (EPA), 4,7,10,13,16,19-docosahexanoic acid (DHA) and 7,10,13,16,19-docosapentaenoic acid (DPA).

As used herein, the term w/w (weight/weight) refers to the amount of a given substance in a composition on weight basis. For example, a composition comprising 50% w/w phospholipids means that the mass of the phospholipids is 50% of the total mass of the composition (i.e., 50 grams of phospholipids in 100 grams of the composition, such as an oil).

As used herein, the terms "food" and "food products" refer to products and ingredients therefore, taken by the mouth, the constituents of which are active in and/or absorbed by the G.I. tract with the purpose of nourishment of the body and its tissues, refreshment and indulgence, which products are to be marketed and sold to customers for consumption by humans. Examples of foods and food and beverage products include, but are not limited to, tea; spreads; ice cream; frozen fruits and vegetables; snacks including diet foods and beverages; condiments; and culinary aids. In some embodiments, a "food" is a material comprising protein, carbohydrate and/or fat, which is used in the body of an organism to sustain growth, repair and vital processes and to furnish energy. Foods may also contain supplementary substances such as minerals, vitamins and condiments. See Merriam-Webster's Collegiate Dictionary, 10th Edition, 1993.

As used herein a "food additive" (e.g., as defined by the FDA in 21 C.P.R. 170.3 (e)(1)) includes direct and indirect additives.

As used herein, a "dietary supplement" is a product that is intended to supplement a diet. In some embodiments, dietary supplements contain little or no calories.

DETAILED DESCRIPTION

Provided herein are compositions and methods for treating, preventing, and reversing malnutrition. In particular, provided herein are compositions and methods for facilitating cognitive repair and preventing obesity (e.g. in children or the elderly).

Existing formulations for prevention or treatment of malnutrition have the specific goal of re-nourishing individuals, in other words returning the amount of nutrients existing within their body to levels that are adequate.

All current commercial and scaled malnutrition formulations include the essential nutrients (e.g., nutrients that are required to prevent death over a period of a few weeks to months) but specifically lack all the nutrients and chemicals noted above that provide for long-term health and cognition. The absence of these additional nutrients hampers restoration of brain and physical function in infants and children who are malnourished or at risk of malnutrition, and instead the usual compositions actually facilitate the poor health and cognitive impairment commonly seen in formerly malnourished individuals.

In contrast, provided herein are compositions and methods that address the need to repair damaged bodily and brain anatomy and function that resulting from malnutrition or being at risk of malnutrition.

The compositions and methods described herein provide the advantage over existing malnutrition products of facilitation of cognitive repair to normalize brain anatomy, and repair cognitive damage including improving such cognitive variables such as attention span, short-term and long-term memory and executive function and reaction time in children or adults who have been malnourished or are at risk of malnutrition. In addition the methods can be used to prevent or reverse cognitive decline associated with aging in older adults who may or may not be malnourished.

The compositions and methods described herein further provide improved short-term and long-term health via improved body composition (more muscle, less fat), reduced inflammation, reduced risk of future obesity.

I. Compositions

Embodiments of the present disclosure provide compositions for preventing and/or treating malnutrition comprising, consisting essentially of, or consisting of one or more of a plurality of flavonoids that cross the blood brain barrier, a plurality of additional flavonoids, omega-3 fatty acids, and caffeine.

In some embodiments, the flavonoids are one or more of catechin, epicatechin, quercetin, and kaempferol. In some embodiments, the flavonoids are catechin and/or epicatechin, alone or in combination with additional flavonoids.

In some embodiments, compositions comprise, consist essentially of, or consist of purified flavonoid compounds (e.g., those described herein). In some embodiments, compositions comprise, consist essentially of, or consist of a food or foods (e.g., fruit, vegetable, leaf, seed, etc. or extracts or fractions thereof) that comprises a flavonoid (e.g., one or more of cocoa, green tea, kale and other green vegetables, tomato, acai berry, blueberry, gingko balboa onion, cherry tomato, cinnamon, or curcumin or extracts or fractions thereof). In some embodiments, compositions comprise cocoa as a source of flavonoids and/or caffeine. The present disclosure is not limited to particular sources of cocoa. The cocoa or cocoa-containing product can be a cocoa powder, such as natural cocoa powder, dutched cocoa powder, extra fine or finely ground cocoa powder having average particle sizes less than 30 microns, high, medium, low fat, defatted, or non-fat cocoa powder, enzyme treated cocoa powder (soluble cocoa) unroasted cocoa powder, underfermented cocoa powder, unfermented cocoa powder, low roasted cocoa powder, heavily roasted cocoa powder, cocoa products produced from unfermented cacao nibs, cocoa products produced from unroasted cacao nibs, any of these products as an extra fine or finely ground cocoa product or powder having average particle sizes less than 30 microns, or less than 10 microns, or even less than 5 microns, and any combination of these cocoa products or powders. In some embodiments, cocoa powder from fermented and heavily roasted, or very dark roast, beans can be used. In addition, various types of defatted or low fat or substantially fat free cocoa powders can used. In some embodiments, the cocoa source has a high flavonoid content.

The cocoa-containing product can also be selected from one or more of: cocoa extracts containing flavanols, baking chocolate, chocolate liquor, cocoa extracts, cacao beans, cacao nibs, cocoa kibble, semisweet chocolate, bittersweet chocolate, and milk chocolate.

In some embodiments, compositions comprise, consist essentially of, or consist of, one or more omega-3 fatty acids that are used for brain myelination. In some embodiments, the omega-3 fatty acids are DHA and/or EPA. In some embodiments, the omega-3 fatty acid is DHA. DHA and EPA are specifically used for structural maintenance and repair of brain and central nervous system tissues. In some embodiments, omega-3 fatty acids are included in formulations in a ratio with omega-6 fatty acids consistent with optimal health.

In some embodiments, purified omega-3 fatty acids are utilized. In some embodiments, compositions (e.g., fish oils) comprising omega-3 fatty acids are utilized. Additional food substances that are rich in omega 3 fatty acids are the fishes halibut, mackerel, salmon, trout, herring and tuna and nutritional plants sources *perilla*, chia seed, flax, and camelina, or algae sources.

In some embodiments, compositions comprise, consist essentially of, or consist of, caffeine or a composition comprising caffeine. Examples of suitable compositions comprising caffeine include, but are not limited to, green tea and cocoa.

In some embodiments, compositions further comprise a plurality of micronutrients. In some embodiments, micronutrients are added to formulations and/or provided as a separate component. These are a differentiator for malnutrition prevention and treatment products. The national and international recommendations for micronutrients are only a subset of the recommended micronutrients for healthy infants. In some embodiments, formulations include the complete range of micronutrients, e.g., including all of those in the DRIs for healthy infants even if those micronutrients are not specifically recommended in malnutrition treatment recommendations (e.g., choline and selenium and chromium).

In some embodiments, the micronutrients, vitamins and/or minerals are one or more of iron, phosphorous, zinc, thiamine, riboflavin, niacin, vitamin B6, folate, vitamin, B12, pantothenic acid, biotin, choline, chromium, copper, manganese, selenium molybdenum, iodine, vitamin A, calcium, potassium, magnesium, vitamin E, vitamin C, a carotenoid, vitamin D, or vitamin K.

In some embodiments, micronutrient levels are generally consistent with nutrient levels recommended by international and national committees on the nutrient requirements of infants and children.

Daily requirements are defined as the higher of 100% of most recent DRIs for the age group the product is designed for, or RNIs (by USAID), multiplied by up to 1.50 for those nutrients which have antinutrients to counterbalance reduced availability (e.g. iron, zinc), with the qualification that the nutrient levels do not generally exceed the nutrient UL specified by DRIs.

In some embodiments, calcium is restricted to less than or equal to 100 mg/d to promote absorption of the other divalent cations. In some embodiments, vitamin E is provided at >DRI to allow for its role in facilitating blood brain barrier passage of certain beneficial flavonoids. In some embodiments, sodium is provided at USAID recommendations. In some embodiments, vitamin A is provided at 50% by Vitamin A and 50% from convertible nutrients such as β-carotene to reduce the risk of excessive Vitamin A intake.

In some embodiments, compositions are lower in sugar and fructose than typical ready-to-use formulations, for specific benefits related to future obesity reduction and modulation of inflammatory processes, which in turn can benefit repair of cognition.

In some embodiments, the concentration of calories and micronutrients in the food depends on its use. For example, in some embodiments, supplementary foods provide a partial daily allowance of calories (e.g. 50 to 500 (e.g., 50, 100, 200, 300, 400, or 500 kcal) to take into account the estimated typical nutrient intakes from a very low quality home diet providing the remaining daily calorie needs.

In some embodiments, therapeutic foods provide the full daily allowance in 100% of the daily calorie needs, because they are the sole or majority food source during acute recovery from malnutrition.

In some embodiments, the composition comprises at least 50 kcal (e.g., at least 50, 100, 200, or 300 kcal).

In some embodiments, the composition comprises approximately 20-35% of it calories from protein, 10-50% of its calories from carbohydrates, and 30-60% of its calories from fat (e.g., approximately 25% of its calories from protein, 30% of its calories from carbohydrates, and 45% of its calories from fat).

In some embodiments, the concentration of calories and micronutrients in the food depends on its use. For example, in some embodiments, supplementary foods provide the fully daily allowance in a proportion of daily calories (e.g. 250 or 300 kcal) minus estimated typical nutrient intakes from a very low quality home diet providing the remaining daily calorie needs.

In some embodiments, therapeutic foods provide the full daily allowance in 100% of the daily calorie needs, because they are the sole or majority food source during acute recovery from malnutrition.

In some embodiments, fortification products provide the full daily allowance of flavonoids, omega-3, most essential micronutrients, +/−animal protein depending on the target population. In this case the calorie content of the fortification is only that which is sufficient to provide the individual named nutrients.

In some embodiments, fiber is provided at naturally occurring values resulting from nutrients, without specific enrichment to meet DRI levels. In other embodiments fiber may be enriched to DRI levels or higher amounts (relative to calories) when acutely preventing or treating obesity would be beneficial.

In some embodiments, electrolytes occur in proportion to kcal in the products and via requirement values for the specific type of product (e.g., therapeutic versus supplementary).

In some embodiment, compositions comprise one or more of protein, fat, or carbohydrates. The present disclosure is not limited to particular sources of nutrients such as protein, fat, and carbohydrates. Animal or plant source of purified (e.g., soy isolate, whey protein, oils, sucrose, fructose, glucose) or natural nutrients are suitable for use in the compositions described herein.

Useful sources of fat include, but are not limited to, extracted or nonextracted fats from meats or vegetables (e.g., butter fat from cream, and other dairy sources, animal fat such as chicken fat or lard, vegetable oil, vegetable shortening, and other vegetable fats such as cocoa butter, illipe, shea, palm, palm kernal, sal, soybean, cottonseed, coconut, rapeseed, canola, and sunflower oils).

Useful sources of protein include, e.g. extracted or non-extracted protein from meats and/or vegetables. For example, a dairy protein source (e.g. whole milk, skim milk, condensed milk, evaporated milk, whey, casein non-fat milk solids). Useful nonextracted sources of protein include, e.g. solid food particles (e. g. meat, fish, or vegetable particles). Useful sources of extracted protein include, e.g. whey, casein, fish, soy protein, egg protein, pea protein, hemp protein, and rice protein.

Useful sources of carbohydrates include, but are not limited to, starchy vegetables such as grains (e.g. whole grain), non-starchy vegetables, vegetables, beans, sucrose, fructose, or honey. Other examples of useful carbohydrate sources include rice, barley, wheat, oats, tubers, potatoes, legumes, nuts, and seeds.

The present disclosure is not limited to specific formulations. Exemplary formulations are provided in Examples 2 and 4 below.

For example, in some embodiments, the composition comprises, consists essentially of, or consists, of cashews, sugar or honey, vegetable oil, raw eggs, a protein mix, high-flavanol cocoa, cinnamon, moringa powder, tomato powder, green tea powder, vitamin powder, and fish oil fortified with fat soluble vitamins or extracts or fractions thereof.

In some embodiments, the composition comprises, consists essentially of, or consists, of 18 g cashews, 3 g sugar or honey, 3.25 g vegetable oil, 4 g raw eggs, 10 g protein mix comprising 4 g whey protein and 6 g soy protein isolate, 5.0 g high-flavanol cocoa, 0.5 cinnamon, 1 g moringa powder, 1.5 g tomato powder, 3.0 g green tea powder, 0.1 g vitamin powder, and 1.7 ml fish oil fortified with fat soluble vitamins per serving or +/−10%, 20%, 30% of any of these values.

In some embodiments, the composition comprises, consists essentially of, or consists, of cashew butter, sorghum flour, vegetable oil, whole eggs, spinach powder, onion powder, moringa powder, tomato powder, green tea powder, turmeric, protein mix, vitamin powder, and fish oil fortified with fat soluble vitamins or extracts or fractions thereof.

In some embodiments, the composition comprises, consists essentially of, or consists, of 20.6 g cashew butter, 6.5 g sorghum flour, 3 g vegetable oil, 1 g whole eggs, 2.8 g spinach powder, 0.2 g onion powder, 1.4 g moringa powder, 1 g tomato powder, 3.7 g green tea powder, 0.2 g turmeric, 21 g protein mix comprising 16 g canned salmon and 5 g soy protein isolate, 0.1 g vitamin powder, and 1.7 ml fish oil fortified with fat soluble vitamins per serving or +/−10%, 20%, 30% of any of these values.

In some embodiments, the composition comprises, consists essentially of, or consists, of cashew butter, sorghum flour, honey, soybean oil, salt, cocoa powder, spinach powder, onion powder, moringa powder, tomato powder, green tea powder, turmeric, protein mix, vitamin powder, and fish oil fortified with fat soluble vitamins or extracts or fractions thereof.

In some embodiments, the composition comprises, consists essentially of, or consists, of 20.6 g cashew butter, 7 g sorghum flour, 4.8 g honey, 3.5 g soybean oil, 0.3 g salt, 4.0 g cocoa powder, 3.0 g spinach powder, 0.2 g onion powder, 1.5 g moringa powder, 1 g tomato powder, 4.0 g green tea powder, 0.2 g turmeric, 20 g protein mix comprising 13 g canned salmon, 1 g egg, and 6 g soy protein isolate, 0.1 g vitamin powder, and 1.7 ml fish oil fortified with fat soluble vitamins per serving or +/−10%, 20%, 30% of any of these values. In some embodiments, the composition comprises, consists essentially of, or consists, of cocoa powder, spinach powder, onion powder, moringa powder, tomato powder, green tea powder, turmeric, salmon powder, soy protein isolate, vitamin powder, and fish oil fortified with fat soluble vitamins or extracts or fractions thereof.

In some embodiments, the composition comprises, consists essentially of, or consists, of 4.0 g cocoa powder, 3.0 g spinach powder, 0.2 g onion powder, 1.5 g moringa powder, 1 g tomato powder, 4.0 g green tea powder, 0.2 g turmeric, 3 g powdered salmon, 6 g soy protein isolate, 0.1 g vitamin powder, and 1.7 ml fish oil fortified with fat soluble vitamins per serving or +/−10%, 20%, 30% of any of these values.

In some embodiments, the composition comprises, consists essentially of, or consists, of cocoa powder, spinach powder, onion powder, moringa powder, tomato powder, green tea powder, turmeric, vitamin powder, and fish oil fortified with fat soluble vitamins or extracts or fractions thereof.

In some embodiments, the composition comprises, consists essentially of, or consists, of 4.0 g cocoa powder, 3.0 g spinach powder, 0.2 g onion powder, 1.5 g moringa powder, 1 g tomato powder, 4.0 g green tea powder, 0.2 g turmeric, 0.1 g vitamin powder, and 1.7 ml fish oil fortified with fat soluble vitamins per serving or +/−10%, 20%, 30% of any of these values.

In some embodiments, the composition comprises, consists essentially of, or consists, of cashew butter, dextrose, soybean oil, cocoa powder, spinach powder, vitamin powder, whey, and fish oil fortified with fat soluble vitamins or extracts or fractions thereof.

In some embodiments, the composition comprises, consists essentially of, or consists, of 20 g cashew butter, 10 g dextrose, 4.0 g soybean oil, 4.0 g cocoa powder, 7.0 g spinach powder, 0.15 g vitamin powder, 4.5 g whey, and 1.9 ml fish oil fortified with fat soluble vitamins per serving or +/−10%, 20%, 30% of any of these values.

In some embodiments, the composition comprises, consists essentially of, or consists, of cocoa powder, spinach powder, green tea powder, vitamin powder, fish protein, soy protein, rice flour, dextrose, soybean oil, and DHA-rich oil fortified with fat soluble vitamins or extracts or fractions thereof.

In some embodiments, the composition comprises, consists essentially of, or consists, of 4.4 g cocoa powder, 5.3 g spinach powder, 2.4 g green tea powder, 0.1 g vitamin powder, 5 g fish protein, 2 g soy protein, 10 g rice flour, 4 g dextrose, 13.4 g soybean oil, and 1.9 ml DHA-rich oil fortified with fat soluble vitamins per serving or +/−10%, 20%, 30% of any of these values.

In some embodiments, the composition comprises, consists essentially of, or consists of cocoa powder, moringa powder, matcha powder, soy protein powder, flaxseed powder, cinnamon, salt, honey, soybutter, raisins, water, whey protein powder, omega 3 oil, chocolate chips, sprinkles, beta carotene, vitamin C, vitamin D, vitamin E, vitamin K, thiamine, riboflavin, niacin, vitamin B6, vitamin B12, pantothenic acid, biotin, choline, chromium, copper, iodine, manganese, molybdenum, selenium, and zinc and optionally iron. In some embodiments, the composition comprises, consists essentially of, or consists of 3.5 g cocoa powder, 0.25 g moringa powder, 0.5 g matcha powder, 5.0 g soy protein powder, 0.5 g flaxseed powder, 0.05 g cinnamon, 0.1 g salt, 2.75 g honey, 8.5 g soybutter, 5.0 g raisins, 7.5 ml water, 2.5 g whey protein powder, 1.71 g omega 3 oil, 2.0 g chocolate chips, sprinkles, 0.00053 g beta carotene, 0.00365 g vitamin C, 0.00000375 g vitamin D, 0.00113 g vitamin E, 0.0000092 g vitamin K, 0.000082 g thiamine, 0.000041 g riboflavin, 0.00125 g niacin, 0.00009 g vitamin B6, 0.00000018 g vitamin B12, 0.00048 g pantothenic acid, 0.0000025 g biotin, 0.0501 g choline, 0.0000033 g chromium, 0.000098 g copper, 0.000018 g iodine, optionally 0.00079 g iron, 0.00036 g manganese, 0.000004 g molybdenum, 0.000005 g selenium, and 0.00030 g zinc per serving or +/−10%, 20%, 30% of any of these values.

In some embodiments, the composition comprises, consists essentially of, or consists of cocoa powder, moringa, matcha, soy protein, whey protein, cinnamon, salt, honey, omega 3 oil, peanut butter, vegetable oil, sugar, vitamin tablet, beta carotene, vitamin C, vitamin D, vitamin E, vitamin K, niacin, vitamin B6, choline, chromium, iodine, magnesium, manganese, molybdenum, selenium, and zinc. In some embodiments, the composition comprises, consists essentially of, or consists of 6.08 g cocoa powder, 0.42 g moringa, 0.83 g matcha, 7.5 g soy protein, 4.3 g whey protein, 0.08 g cinnamon, 0.13 g salt, 8 g honey, 1.42 g omega 3 oil, 13.8 g peanut butter, 5.83 g vegetable oil, 3.5 g sugar, 1.14 g vitamin tablet, 0.00018 g beta carotene, 0.0937 g vitamin C, 0.0000046805 vitamin D, 0.011 g vitamin E, $1.51 \times 10^{-6}$ g vitamin K, 0.00865 g niacin, 0.000118 g vitamin B6, 0.0381 g choline, 0.000000015 g chromium, 0.000033 g iodine, 0.0176 g magnesium, 0.0015 g manganese, 0.0000225 g molybdenum, $3.85 \times 10^{-5}$ g selenium, and 0.00297 g zinc per serving or 7.3 g cocoa powder, 0.5 g moringa, 1.0 g matcha, 9.0 g soy protein, 5.2 g whey protein, 0.1 g cinnamon, 0.15 g salt, 9.5 g honey, 1.71 g omega 3 oil, 16.5 g peanut butter, 7.0 g vegetable oil, 4.2 g sugar, 1.14 g vitamin tablet, 0.0939 g vitamin C, 0.000004 g vitamin D, 0.011 g vitamin E, 0.00004 g vitamin K, 0.003 g niacin, 0.0001 g vitamin B6, 0.022 g choline, 0.00000002 g chromium, 0.000033 g iodine, 0.00153 g manganese, 0.0000225 g molybdenum, and 0.00334 g zinc per serving or +/−10%, 20%, 30% of any of these values.

The amounts of each component are scaled based on serving size and age of the subject.

The present disclosure is not limited to a particular formulation comprising one or more of the above-described compositions. In some embodiments, compositions are provided as one or more of supplements, food products, foods, and food additives. In some embodiments, foods and food products are one or more of bars (e.g., raw bars), biscuits, crackers, chips, pastes, gruels and liquids beverages, powders, and the like.

In some embodiments, compositions are shelf-stable or fresh versions of ready-to-use supplementary foods (RUSF), which can be single products or combinations of more than one product that together provide the complete formulation; ready-to-use therapeutic foods (RUTF); which can be single products or combinations of more than one product that together provide the complete formulation; mixes (e.g., powders or pastes) that are used as a composite ingredient to create RUTF and RUSF when combined with local ingredients in countries where malnutrition is prevalent; mixes (e.g., powders or pastes) that are used by individual households to fortify local food preparations.

In some embodiments, compositions are provided as supplement pills that are used to supplement a diet that is fundamentally adequate in macronutrients but lacking in flavonoids and/or omega-3 fatty acids and/or caffeine and essential nutrients for restoration of mental and physical function following malnutrition or being at risk of malnutrition.

In some embodiments, the present disclosure provides a supplement composition comprising one or more of the foregoing compositions in combination with a pharmaceutically acceptable carrier. The actual form of the carrier, and thus, the composition itself, is not critical. The carrier may be a liquid, gel, gelcap, capsule, powder, solid tablet (coated caplet or non-coated), tea, or the like. The composition, in this case, is preferably in the form of a tablet or capsule and most preferably in the form of a soft gel capsule. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof. The various ingredients and the excipient and/or carrier are mixed and formed into the desired form using conventional techniques. The tablet or capsule may be coated with an enteric coating that dissolves at a pH of about 6.0 to 7.0. A suitable enteric coating that dissolves in the small intestine but not in the stomach is cellulose acetate phthalate. Further details on techniques for formulation for and administration may be found in the latest edition of Remington's Pharmaceutical Sciences (Maack Publishing Co., Easton, PA).

The dietary supplement may comprise one or more inert ingredients, especially if it is desirable to limit the number of calories added to the diet by the dietary supplement. For example, the dietary supplement may also contain optional ingredients including, for example, herbs, vitamins, minerals, enhancers, colorants, sweeteners, flavorants, inert ingredients, and the like.

In further embodiments, the compositions comprise at least one food flavoring such as acetaldehyde, acetoin (acetyl methylcarbinol), anethole (parapropenyl anisole), benzaldehyde (benzoic aldehyde), N butyric acid (butanoic acid), d or 1 carvone (carvol), cinnamaldehyde (cinnamic aldehyde), citral (2,6 dimethyloctadien 2,6 al 8, gera nial, neral), decanal (N decylaldehyde, capraldehyde, capric aldehyde, caprinaldehyde, aldehyde C 10), ethyl acetate, ethyl butyrate, 3 methyl 3 phenyl glycidic acid ethyl ester (ethyl methyl phenyl glycidate, strawberry aldehyde, C 16 aldehyde), ethyl vanillin, geraniol (3,7 dimethyl 2,6 and 3,6 octadien 1 ol), geranyl acetate (geraniol acetate), limonene (d, 1, and dl), linalool (linalol, 3,7 dimethyl 1,6 octadien 3 ol), linalyl acetate (bergamol), methyl anthranilate (methyl 2 aminobenzoate), piperonal (3,4 methylenedioxy benzaldehyde, heliotropin), vanillin, alfalfa (*Medicago sativa* L.), allspice (*Pimenta officinalis*), ambrette seed (*Hibiscus abelmoschus*), angelic (*Angelica archangelica*), Angostura (*Galipea officinalis*), anise (*Pimpinella anisum*), star anise (*Illicium verum*), balm (*Melissa officinalis*), basil (*Ocimum basilicum*), bay (*Laurus nobilis*), calendula (*Calendula officinalis*), (*Anthemis nobilis*), capsicum (*Capsicum frutescens*), caraway (*Carum carvi*), cardamom (*Elettaria cardamomum*), cassia, (*Cinnamomum cassia*), cayenne pepper (*Capsicum frutescens*), Celery seed (*Apium graveolens*), chervil (*Anthriscus cerefolium*), chives (*Allium schoenoprasum*), coriander (*Coriandrum sativum*), cumin (*Cuminum cyminum*), elder flowers (*Sambucus canadensis*), fennel (*Foeniculum vulgare*), fenugreek (*Trigonella foenum graecum*), ginger (*Zingiber officinale*), horehound (*Marrubium vulgare*), horseradish (*Armoracia lapathifolia*), hyssop (*Hyssopus officinalis*), lavender (*Lavandula officinalis*), mace (*Myristica fragrans*), marjoram (*Majorana hortensis*), mustard (*Brassica nigra, Brassica juncea, Brassica hirta*), nutmeg (*Myristica fragrans*), paprika (*Capsicum annuum*), black pepper (*Piper nigrum*), peppermint (*Mentha piperita*), poppy seed (*Papayer somniferum*), rosemary (*Rosmarinus officinalis*), saffron (*Crocus sativus*), sage (*Salvia officinalis*), savory (*Satureia hortensis, Satureia montana*), sesame (*Sesamum indicum*), spearmint (*Mentha spicata*), tarragon (*Artemisia dracunculus*), thyme (*Thymus vulgaris, Thymus serpyllum*), turmeric (*Curcuma longa*), vanilla (*Vanilla planifolia*), zedoary (*Curcuma zedoaria*), sucrose, glucose, saccharin, sorbitol, mannitol, aspartame. Other suitable flavoring are disclosed in such references as Remington's Pharmaceutical Sciences, 18th Edition, Mack Publishing, p. 1288-1300 (1990), and Furia and Pellanca, Fenaroli's Handbook of Flavor Ingredients, The Chemical Rubber Company, Cleveland, Ohio, (1971), known to those skilled in the art.

In other embodiments, the compositions comprise at least one synthetic or natural food coloring (e.g., annatto extract, astaxanthin, beet powder, ultramarine blue, canthaxanthin, caramel, carotenal, beta carotene, carmine, toasted cottonseed flour, ferrous gluconate, ferrous lactate, grape color extract, grape skin extract, iron oxide, fruit juice, vegetable juice, dried algae meal, tagetes meal, carrot oil, corn endosperm oil, paprika, paprika oleoresin, riboflavin, saffron, tumeric, tumeric and oleoresin).

In some embodiments, combinations of different supplement pills or combinations of food products and supplements are used to provide complete compositions.

In some embodiments, commercial or home kitchens or laboratories are used to ensure food safety and prevention of nutrient degradation during storage, including the addition of necessary preservatives and additives and (for shelf-stable products) microbial testing as required by food safety regulations. In some embodiments, compositions are low in water content to achieve microbial safety.

II. Uses

The compositions and foods described herein find use in a variety of applications related to treating and preventing malnutrition. In some embodiments, one or more of the compositions (e.g., a single supplement, a single food, a combination of a supplement and a food, or a combination of multiple foods and beverages) is administered to a subject in need thereof (e.g., a subject suffering from malnutrition or a risk of malnutrition). In some embodiments, the subject is suffering from malnutrition not caused by a wasting disease or condition. In some embodiments, the subject has been suffering from malnutrition for at least one week (e.g., at least one week, one month, one year, etc.)

In some embodiments, the subject has reduced cognitive function relative to an age-matched subject not suffering from malnutrition (e.g., a population average of the same or a different community or ethnic group). In some embodiments, the subject does not have reduced cognitive function. In some embodiments, the subject has reduced cognitive function related to malnutrition.

In some embodiments, subjects are children (e.g., under the age of 18, under the age of 12, under the age of 10, under the age of 6, under the age of 4, or under the age of 2). In some embodiments, subjects are 2-8 years old (e.g., 2-6, 2-7, 2-5, 2-4, or 2-3 years old. In some embodiments, the subject is not an adult.

In some embodiments, subjects are elderly adults (e.g., older than 50, 60, 70, 80, or 90 years) and the administration of the composition prevents or reverses cognitive decline associated with aging.

In some embodiments, the subject is a pregnant woman and the administration of the compositions described herein prevents malnutrition and malnutrition associated cognitive function in the developing embryo or fetus before and/or after birth.

In some embodiments, one or more servings of the composition is administered one or more times a day (e.g., as a supplement or meal replacement) for a period of several days to several years (e.g., several days, one week, several weeks, one month, several months, one year, or several years). In some embodiments, the composition is administered until malnutrition is resolved. In some embodiments, the composition is administered until cognitive function is improved to the level of a subject not suffering from malnutrition. In some embodiments, administration of the compositions and foods described herein improves the cognitive function of the subject (e.g., to the level of a subject not suffering from malnutrition). In some embodiments, the administration of the compositions and foods described herein repairs cognitive damage caused by malnutrition. In some embodiments, the administration of the compositions and foods described herein prevents cognitive damage caused by malnutrition.

EXPERIMENTAL

Example 1

Clinical Study

This Example describes a clinical study for assessing nutritional formulations of embodiments of the present disclosure for products suitable for prevention of malnutrition.

Up to 20 children aged 24-30 months and 20 school children aged 6-6.5 years living in each of 2 villages (total study population up to 80, with no minimum recruitment number) are recruited for this study, with ages documented by the official birth record, which all families possess. Villages are a convenience sample chosen from villages within the network of the local research partner International Partnership for Human Development. Each village in this region has one school and one community health center per village, which are involved in supplement distribution and some outcome assessments. The villages are broadly comparable in terms of size, affluence, rates of malnutrition, the presence or absence of a school meal program, and tribal affiliation and religion.

One village is randomly assigned to receive the locally-prepared biscuit and a daily multivitamin and the other is randomly assigned to be an assessment-only control site. The randomization occurs prior to baseline testing. Villagers are not informed of the randomization until after baseline testing is complete.

Following baseline measurements of anthropometry, grip strength, cognition, non-invasive measurements of hemoglobin, skin carotenoids and cerebral hemodynamic and oxygen metabolism (assessed with non-invasive near infrared spectroscopy, NIRS), participants receive their intervention for 12 weeks and the same measurements taken at baseline are repeated during the last study week. The trial is terminated between 9-12 weeks of supplement consumption depending on weather conditions.

The Supplement

The intervention is a locally prepared biscuit with low sugar content (less than 10% dry weight) designed to facilitate growth and cognitive development, and is provided to participants 5 days a week during the study period together with a multivitamin (collectively termed the "supplement"; see exemplary formulations in Example 2). Because the multivitamin contains only those nutrients commonly found in food, the combination of the biscuit and the multivitamin is considered to be food collectively considered. The biscuit provides 250-300 kcal/day and has ≈20-30% of energy from protein (of which 25-50% is from an animal protein source), 20-35% from total carbohydrate and ≈40-60% from fat (with final composition in these ranges to be determined by local product acceptability testing). In addition the biscuit is fortified with vitamins and minerals so that the combination of the biscuit and the multivitamin meets USAID recommendations for moderate malnutrition (Webb et al. 2011, Delivering Improved Nutrition: *Recommendations for Changes to U.S. Food Aid Products and Programs*. Boston, MA: Tufts University) and Dietary Reference Intake (Institute of Medicine, 2015) recommendations for at-risk and healthy children of the ages studied, and at the same time will not exceed Upper Level nutrient recommendations for any micronutrient (Institute of Medicine, 2015).

Ingredients in the biscuit are a combination of local products that are routinely consumed in the villages and imported ingredients that are shelf-stable and commercially available in the U.S. The local ingredients may include any of the following: groundnuts, cashews, sorghum, rice, eggs, honey. The imported ingredients may include any of the following: fat-free milk powder, dried whey, dried whole egg, canned salmon and sardines, cricket flour, wheat flour, sugar, sorghum, millet, soy oil, fish oil, cinnamon, turmeric, cocoa, green tea, dried green vegetables such as spinach, kale and moringa, flax seed meal, chia seed meal, soy flour, soy protein extract, and legume flours, and individual vitamins and minerals needed for biscuit fortification. Proportions of ingredients are determined by the nutrient composition metrics and acceptability tests. Some of these foods contain caffeine, and the caffeine content of the biscuits is <5 mg/kg body weight/d, which has been reported to be a safe level even in much more vulnerable populations such as preterm infants (Mueni et al. 2009, Int Health 2009; 1:190-5). The imported ingredients are imported specifically for the study from the U.S. and stored under refrigeration in Bissau and delivered to the bakers weekly in pre-measured amounts for biscuit production.

The specific recipes for the supplements are developed by collaboration between investigators and local villagers. Prior to the trial several variants of locally prepared biscuits are developed with consideration of available ingredients and local taste preferences. Once these initial variants have been prepared, taste tests are held to determine which variants are most acceptable to village members. The village leaders identify possible villagers to participate in this test, participation is voluntary, and no participant identifiers are recorded. Once final supplement recipes (1 or more depending on which are acceptable) have been selected, local commercial bakers prepare the supplements 5 days per week during the trial, using locally accepted standards for hygiene, and a quality control process for ratios of ingredients assigned by the research team to ensure consistent composition of the biscuits. Samples of the biscuits are saved and stored frozen for return to the U.S for composition testing.

Intervention

School children (age 6 to 6.5) receive their supplement 5 days a week in the morning before school starts. They either receive the supplement at school or at the community health center depending on the preference of the villagers after recruitment. Young children (age 24 to 30 months) receive the supplement 5 days a week in the morning at the community health center, distributed by community health workers. This age group universally consumes solid foods, and have usually finished breastfeeding. Nevertheless some of the children may still prefer eating semi-solid food, and mothers have the option of mashing the biscuits and mixing it with water if they prefer.

The teachers and community health workers record supplement consumption daily during the study, and report the information weekly to the local research team. Parents of participants in the active intervention are counseled to not reduce the regular food intake of their child, so that the supplement is additive rather than substituting for home food.

Control

The control is assessment only.

Outcomes

All outcomes are measured at baseline and during the last week of the intervention in the morning on a day when the child is well. If the child cannot be tested at this time, measurements are taken not later than 2 weeks after this date. Because breakfast is not typically consumed in this community and the supplement is provided in the morning, measurements at the end of the study is standardized in relation to timing of morning supplement consumption. During measurements direct contact with participants is by local research staff and nurses from the Ministry of Education.

Weight and Height

Duplicate measurements of weight to ±0.1 kg are taken using a calibrated digital scale (e.g. floor scale model 813, Seca, Chino, CA). Duplicate measures of height are made with an upright stadiometer measuring to 0.1 cm (e.g. models 213, Seca, Chino CA).

Circumferences

Duplicate measurements of mid-upper arm circumference (MUAC) are taken at the midpoint between the acromion process of scapula and olecranon process, and head circumference are measured in duplicate at the widest diameter, using standardized WHO methods.

Hand Grip Strength

In the children aged 6-6.5 years, grip strength in both hands is measured in duplicate using a dynamometer suitable for pediatric populations (e.g. Lode BV, Amsterdam. The Netherlands). Participants are asked to squeeze the lever as hard as they can three times to obtain readings within 10% of each other, sitting in a position with the shoulder adducted, the elbow flexed in a 90° angle, and the wrist in a neutral position (Molenaar et al 2010, Clin Orthop Relat Res. 2010; 468:217-223).

Child Cognitive Testing

Tests are cultural adaptations of standard assessments (Carlson et al. 2004; Kochanska et al. 1990, Dev Psychol 2004; 40:1105-22; Weschler 1989, Wechsler Preschool and Primary Scale of Intelligence—Revised. San Antonio, TX: The Psychological Corporation) focusing on children's executive function (e.g., how long children can wait to look for a toy inside a box or bag, how easily children learn a new rule for sorting objects or identifying images), short-term memory (e.g., remembering which locations they have checked while searching for a hidden object), attention (e.g., searching for an image among a display of distractor items), rate of habituation (e.g., how quickly children become uninterested in a new toy), and spatial reasoning (e.g., forming shapes with blocks, putting together puzzles). Individual tasks are designed to be culturally appropriate short games involving small household or other familiar objects, toys, puzzles, and pictures, and last less than 15 minutes in total. Children sit on their caregiver's lap or next to their caregiver in a seat. A parent decides where the child is most comfortable participating—in their lap or seated beside them. If children become fussy or upset, the researcher stops the assessment, and caregivers can also ask to stop the study at any time. Children's behaviors are coded from the video recordings at a later time.

Hemoglobin

Hemoglobin is measured non-invasively using a standard technique that uses light of different wavelengths directed at the finger (Causey et al 2011, Am J Surg 2011; 201: 592-8) (Pronto 7, Masimo Corporation Irving CA).

Skin Carotenoids

Resonance Raman Spectroscopy (RRS) is a non-invasive optical measure of carotenoids in tissue, measured by shining light in the palm of the hand (Hata et al 2000, J Invest Dermatology 2000; 114:441-8). This site is convenient not only for accessibility, but also for the following reasons: (i) the carotenoid concentration in the palm is among the highest found in skin (because carotenoids are lipophilic and palm skin has a high lipid/protein ratio), (ii) differences in pigmentation among various skin types are minimal in the palm, and (iii) the stratum corneum thickness of the palm (~400 μm) is high compared with other skin sites. With a NuSkin scanner (Pharmanex Global Research, UT), a laser power of <10 mW and an exposure time of 30 seconds per measurement with an elliptical spot size of 2 mm by 3 mm is used. The RRS uses a class 2-B laser (National Laser Inc, Salt lake City, UT) and with this laser power and spot size it is safe to expose skin for up to 30,000 seconds (Ermakov et al 2004; Mayne et al 2010). Two measurements are taken in each hand.

Cerebral Hemodynamics and Oxygen Metabolism with NIRS

Cerebral hemodynamics, including blood volume (CBV) and blood flow (CBF), and cerebral metabolic rate of oxygen ($CMRO_2$), are estimated non-invasively with light via the forehead of enrolled children. Advanced near-infrared spectroscopy (NIRS) technology developed by Dr. Franceschini and her team (Lin et al. 2013, J Vis Exp 2013; E4379) at the Optics Division of the Athinoula A. Martinos Center for Biomedical Imaging, Massachusetts General Hospital (Boston, MA) is used. These NIRS devices have been successfully used without any risk in more than 400 infants children at Massachusetts General Hospital, Brigham and Women Hospital, and Boston Children's Hospital and in more 40 children at the Cure Children's Hospital in Uganda.

Diffuse Correlation Spectroscopy (DCS) devices are used to obtain an index of blood flow and an index of hemoglobin concentration. The blood flow in deep tissue is obtained by quantifying the temporal intensity fluctuations of scattered light that arise from Doppler shifts induced by moving red blood cells. The hemoglobin concentration is obtained by measuring light attenuation induced by tissue absorption. DCS devices consist of a long-coherence length at a wavelength between 750 and 850 nm, 4 to 8 low dark-count photon counting avalanche photodiodes, and a custom-made correlator board. For this project, two DCS devices at different wavelengths are optionally used (operated simultaneously by alternating the two light sources on and off).

A frequency-domain (FD) NIRS device is optionally used in parallel to the DCS systems. This FDNIRS prototype has been built by ISS, Inc. in collaboration with Dr. Franceschini group at MGH. The FDNIRS device consists of 8 radio frequency (110 MHz) modulated laser diodes operating at 8 different wavelengths ranging from 670-830 nm and up to 4 photomultiplier tube detectors (PMT) for heterodyne detection.

The light from/to the DCS and FDNIRS devices is delivered to/from the head of the subject through fiber optic cables arranged within an optical sensor. The optical fibers are flexible and plug into 90-degree angle prisms so the fibers lie flat against the head. The prisms are arranged on a square or rectangular rubber sensor of a size no larger than 30 $cm^2$. The DCS and FDNIRS lights are turned on in sequence during data acquisition. At any time, approximately 50-70 mW of laser light illuminates the skin diffusely over a 5 mm spot. This result in less than 0.3-0.4 $W/cm^2$ exposure to the skin, within the ANSI Standards approved light levels (0.4 $W/cm^2$ at 850 nm). The laser light is not collimated, but rather is expanded/diffused at the end of the fiber, and diverges in a very wide angle (>50 deg) at the probe end. This results in an NOHD of 5-7 cm, which is lower than the 10 cm focusing distance of the retina. Hence, eye protection is not required.

During each measurement session an operator holds the NIRS sensor in position on the forehead of the child for 10-20 seconds. NIRS measurements are done in up to 4 locations in the forehead and repeated up to 7 times in each location, for a total time not longer than 10-15 minutes. Lasers are turned on only when the optical sensor is in position and are turned off whenever the sensor must be lifted. In addition, trained investigators handle the sensor as if the lasers are on and take precautions to make sure the sensor is never pointed towards the child's eyes. The optical sensor is sanitized with germicidal disposable wipes (super-sani-cloth, PDI) before and after use in each child.

Food Product Acceptability

Mothers (for the young children) and school children are asked on a 4-point scale of 'not at all' 'a little', 'moderately' and 'very much' how much they enjoy eating the biscuits and the multivitamin.

Mother's Anthropometry

In order to evaluate the results obtained in children in relation to individual family circumstances, the weight, height and MUAC of the mothers is also measured, and family demographic data (family size, number of wives and children and ages) is collected by questioning the mother.

Photographs

Parents (and children, in the case of the school children) are asked for permission to take photographs of them that illustrate the outcome measurements and supplement consumption, for the purpose of using in presentations on the research.

Data Management and Statistical Analyses

De-identified data is entered into a password-protected secure database by the local Guinea Bissau team prior to transmission by email to U.S.-based collaborators. The de-identifying code linking identifiers are kept in a secure environment by the PI. All photographs and videotapes are stored without names or other written identifiers of the individuals.

Child Eligibility

Eligibility is assessed by the local research team in collaboration with health center and school officials. Non-malnourished children within the 2 villages chosen for study are eligible to participate if they meet the following inclusion criteria:

They are within the specified age range: 24-30 months for young children and 6-6.5 years for older children, who are also be enrolled in their local school.

The family plans to remain in the village for the duration of the study;

The child does not have any known food allergies as reported by the mother or guardian.

This study concerns products for prevention of malnutrition. Therefore, if any child is identified as malnourished at baseline, defined as a mid-upper arm circumference in the red zone of the paper tape or a weight-for-age or height-for-age z-score of less than or equal to −3.0, the child is excluded from the study due to malnutrition, and the parents are advised to take the child to the nearest malnutrition clinic.

Location of Research

Two villages of comparable size and affluence, with equivalent rates of malnutrition based on previous surveys, and both either with or without a current school lunch program, and of the same tribe and religion in the region of Oio, Guinea-Bissau. All intervention activities are conducted in the villages. Outcomes testing is conducted partly in the villages (e.g. records of adverse events) and also in a quiet room in the regional health clinic in the local town of Bissora, where children and their mothers are transported for outcomes testing at the beginning and end of the study period.

Example 2

Formulations

This example describes exemplary formulations of embodiments of the present disclosure. Additional formulations and ingredients can also be utilized.

1. Ready-to-Use-Supplementary Biscuit for 2-Year Old Child

This recipe makes 1 individual daily supplement and is multiplied up as needed (See Table 1 for nutritional information).

Ingredients 18 g cashews ground into paste 3 g sugar or honey 3.25 g mix vegetable oils such as soybean canola corn etc.

4 g whole raw egg 10 g protein mix 2 (4 g whey protein, 6 g soy protein isolate)

11.1 g FCV-1 (flavonoid/caffeine/vitamin-mineral dry mix #1): 5.0 g high-flavanol cocoa; 0.5 g cinnamon; 1 g moringa powder; 1.5 g tomato powder; 3.0 g green tea powder; 0.1 g vitamin/mineral powder 1.7 ml DHA-rich fish oil fortified with fat-soluble vitamins to meet daily targets.

Instructions

Ingredients are measured out and mixed together with sufficient water to form a dough, portioned out in individual servings, shaped into cookie round and then baked until cooked, approximately 14 minutes at 350 F.

Biscuits are stored in clean container before consumption. The same recipe with adaptations well known to commercial food companies can be turned into a shelf-stable bar for mass production.

TABLE 1

| Constituent | Units | Total daily nutrient target | Daily intake from home food | Daily intake from supplement 1 (biscuit) |
| --- | --- | --- | --- | --- |
| Energy | kcal | 956 | 656 | 249 |
| Protein | g | 23 | 11.7 | 12.9 |
| Protein from animal sources | g | | 0 | 3.75 |
| Fat | % energy | 20-60% | 5% | 51.3% |
| Carbohydrate | % energy | 20-60% | 86% | 34% |
| Fructose | % energy | <10% | — | <10% |
| Iron | mg | 9 | 2.0 | 7 |
| Magnesium | mg | 190 | 90 | 100 |
| Phosphorous | mg | 570 | 214 | 161 |
| Zinc | mg | 12 | 2 | 10 |
| Vit C | mg | 70 | 29 | 41 |
| Thiamine (B1) | mg | 0.575 | 0.23 | 0.35 |
| Riboflavin (B2) | mg | 0.77 | 0.13 | 0.64 |
| Niacin | mg | 8 | 3 | 5 |
| Vit B6 | mg | 0.77 | 0.34 | 0.43 |
| Vit B9 (folate) | µg | 210 | 73 | 137 |
| Vit B12 | µg | 0.77 | 0 | 0.77 |
| Vit A | RE, µg | 920 | 13 | 907 |
| Vit E | mg | 16.5 | 0.7 | 15.9 |
| Vit D | µg | 7 | 0 | 7 |
| Vit K | µg | 30 | 5 | 25 |
| Vit B5 (pantothenic acid) | mg | 3 | 2 | 1 |
| Vit B7 (biotin) | mg | 9.5 | 0 | 9.5 |
| Choline* | mg | 200 | 31 | 169 |
| Chromium* | µg | 11 | 0 | 11 |
| Copper | mg | 650 | 0 | 650 |
| Manganese | mg | 1.2 | 1.9 | 0.5 |
| Selenium* | µg | 20 | 21 | 8.3 |
| Molybdenum | µg | 17 | 0 | 17 |
| Iodine | µg | 90 | 0 | 90 |
| Omega-3 | g | 0.1-2.0 | 0.1 | 671 |
| EPA + DHA* | mg | 300-500 | 0 | 545 |
| Caffeine* | mg | 40 | N/A | 27 |

TABLE 1-continued

| Constituent | Units | Total daily nutrient target | Daily intake from home food | Daily intake from supplement 1 (biscuit) |
| --- | --- | --- | --- | --- |
| Flavanoids* | mg | 20-2000 | N/A | 838 |
| Flavanols* | mg | 200-500 | N/A | 394 |

Bold indicates higher target intake than currently recommended by international committees for malnutrition treatment/prevention.
Bold* indicates that current malnutrition treatment/prevention recommendations by USAID have no requirement value.
N/A data not available, anticipated very low values.
Electrolytes (sodium, potassium, chloride) included in recommended amounts.

2. Ready-to-Use-Supplementary Biscuit Plus Multivitamin for 2-Year Old Child

This recipe makes 1 individual daily supplement and is multiplied up as needed (See Table 2 for nutritional information).

Biscuit Ingredients 18 g cashews ground into paste 3 g sugar or honey 3.25 g mix vegetable oils such as soybean canola corn etc.

4 g whole raw egg 10 g protein mix 2 (4 g whey protein, 6 g soy protein isolate)

11.1 g FCV-1 (flavanoid/caffeine/vitamin-mineral dry mix #1): 5.0 g high-flavanol cocoa; 0.5 g cinnamon; 1 g moringa powder; 1.5 g tomato powder; 3.0 g green tea powder 1.7 ml DHA-rich fish oil fortified with fat-soluble vitamins to meet daily targets.

Custom multivitamin(s) (chewable for this age group) to provide essential daily vitamins and minerals not consumed as part of home food and the biscuit supplement.

Instructions

Biscuit ingredients are measured out and mixed together with sufficient water to form a dough, portioned out in individual servings, shaped into cookie round and then baked until cooked, approximately 14 minutes at 350 F.

Biscuits are stored in clean container before consumption. The same recipe with adaptations well known to commercial food companies can be turned into a shelf-stable bar for mass production.

The supplement is the biscuit plus the multivitamin.

TABLE 2

| Constituent | Units | Total daily nutrient target | Daily intake from home food | Daily intake from supplement (biscuit + multivitamin) |
| --- | --- | --- | --- | --- |
| Energy | kcal | 956 | 656 | 250 |
| Protein | g | 23 | 11.7 | 12.9 |
| Protein from animal sources | g | | 0 | 3.75 |
| Fat | % energy | 20-60% | 5% | 51.3% |
| Carbohydrate | % energy | 20-60% | 86% | 34% |
| Fructose | % energy | <10% | — | <10% |
| Iron | mg | 9 | 2.0 | 7 |
| Magnesium | mg | 190 | 90 | 100 |
| Phosphorous | mg | 570 | 214 | 161 |
| Zinc | mg | 12 | 2 | 10 |
| Vit C | mg | 70 | 29 | 41 |
| Thiamine (B1) | mg | 0.575 | 0.23 | 0.35 |
| Riboflavin (B2) | mg | 0.77 | 0.13 | 0.64 |
| Niacin | mg | 8 | 3 | 5 |
| Vit B6 | mg | 0.77 | 0.34 | 0.43 |
| Vit B9 (folate) | µg | 210 | 73 | 137 |
| Vit B12 | µg | 0.77 | 0 | 0.77 |

TABLE 2-continued

| Constituent | Units | Total daily nutrient target | Daily intake from home food | Daily intake from supplement (biscuit + multivitamin) |
|---|---|---|---|---|
| Vit A | RE, μg | 920 | 13 | 907 |
| Vit E | mg | 16.5 | 0.7 | 15,9 |
| Vit D | μg | 7 | 0 | 7 |
| Vit K | μg | 30 | 5 | 25 |
| Vit B5 (pantothenic acid) | mg | 3 | 2 | 1 |
| Vit B7 (biotin) | mg | 9.5 | 0 | 9.5 |
| Choline* | mg | 200 | 31 | 169 |
| Chromium* | μg | 11 | 0 | 11 |
| Copper | mg | 650 | 0 | 650 |
| Manganese | mg | 1.2 | 1.9 | 0.5 |
| Selenium* | μg | 20 | 21 | 8.3 |
| Molybdenum | μg | 17 | 0 | 17 |
| Iodine | μg | 90 | 0 | 90 |
| Omega-3 | g | 0.1-2.0 | 0.1 | 671 |
| EPA + DHA* | mg | 300-500 | 0 | 545 |
| Caffeine* | mg | 40 | N/A | 27 |
| Flavanoids* | mg | 20-2000 | N/A | 838 |
| Flavanols* | mg | 200-500 | N/A | 394 |

Bold indicates higher target intake than currently recommended by international committees for malnutrition treatment/prevention.
Bold* indicates that current malnutrition treatment/prevention recommendations by USAID have no requirement value.
N/A data not available, anticipated very low values.
Electrolytes (sodium, potassium, chloride) included in recommended amounts.

3. Combination of a Biscuit and Drink for 2-Year Old Child

This recipe makes 1 individual daily supplement and is multiplied up as needed (See Table 3 for nutritional information).

Biscuit Ingredients 20.6 g cashew butter 6.5 g sorghum flour 3 g soybean or other oil 1 g whole egg 9.4 g FCV-3 (flavinoid/caffeine/vitamin-mineral dry mix #3): 2.8 g spinach powder; 1.4 g Moringa powder, 0.2 g onion powder, 1 g tomato powder; 0.2 g turmeric; 3.7 g green tea powder; 0.1 g vitamin/mineral powder 21 g protein mix 2 (16 g canned salmon; 5 soy protein isolate)

1.7 ml DHA-rich fish oil fortified with fat-soluble vitamins

Chocolate Drink Ingredients 3 g nonfat dried milk 2.3 g honey 5 g high-flavanol cocoa powder Instructions Biscuit ingredients are measured out and mixed together with sufficient water to form a dough, portioned out in individual servings, shaped into cookie round and then baked until cooked, approximately 12 minutes at 350 F.

Biscuits are stored in clean container before consumption.

Drink ingredients are mixed together and then mixed with 8 oz boiled water, adding a small amount of the water first to form a smooth paste before adding remainder of water.

Biscuit and drink combined are the daily supplement.

TABLE 3

| Constituent | Units | Total daily nutrient target | Daily intake from home food | Daily intake from Biscuit and Drink |
|---|---|---|---|---|
| Energy | kcal | 956 | 656 | 299 |
| Protein | g | 23 | 11.7 | 12.75 |
| Protein from animal sources | g | | 0 | 3.7 |
| Fat | % energy | 20-60% | 5% | 55% |
| Carbohydrate | % energy | 20-60% | 86% | 31.9% |
| Fructose | % energy | <10% | — | <10% |
| Iron | mg | 9 | 2.0 | 7.0 |
| Magnesium | mg | 190 | 90 | 100 |
| Phosphorous | mg | 570 | 214 | 237 |
| Zinc | mg | 12 | 2 | 10 |
| Vit C | mg | 70 | 29 | 41 |
| Thiamine (B1) | mg | 0.575 | 0.23 | 1.1 |
| Riboflavin (B2) | mg | 0.77 | 0.13 | .64 |
| Niacin | mg | 8 | 3 | 5 |
| Vit B6 | mg | 0.77 | 0.34 | .40 |
| Vit B9 (folate) | μg | 210 | 73 | 137 |
| Vit B12 | μg | 0.77 | 0 | .47 |
| Vit A | RE, μg | 920 | 13 | 907 |
| Vit E | mg | 16.5 | 0.7 | 15.9 |
| Vit D | μg | 7 | 0 | 7 |
| Vit K | μg | 30 | 5 | 25 |
| Vit B5 (pantothenic acid) | mg | 3 | 2 | 1 |
| Vit B7 (biotin) | mg | 9.5 | 0 | 9.5 |
| Choline* | mg | 200 | 31 | 169 |
| Chromium* | μg | 11 | 0 | 11 |
| Copper | mg | 650 | 0 | 649 |
| Manganese | mg | 1.2 | 1.9 | .5 |
| Selenium* | μg | 20 | 21 | 9 |
| Molybdenum | μg | 17 | 0 | 17 |
| Iodine | μg | 90 | 0 | 90 |
| Omega-3 | g | 0.1-2.0 | 0.1 | 826 |
| EPA + DHA* | mg | 300-500 | 0 | 545 |
| Caffeine* | mg | 40 | N/A | 30.2 |
| Flavanoids* | mg | 20-2000 | N/A | 1066 |
| Flavanols* | mg | 200-500 | N/A | 609 |

Bold indicates higher target intake than currently recommended by international committees for malnutrition treatment/prevention.
Bold* indicates that current malnutrition treatment/prevention recommendations by USAID have no requirement value.
N/A data not available, anticipated very low values.
Electrolytes (sodium, potassium, chloride) included in recommended amounts.

4. Ready-to-Use-Supplementary Biscuit for 5-Year Old Child

This recipe makes 1 individual daily supplement and is multiplied up as needed (See Table 4 for nutritional information).

Ingredients 20.6 g cashew butter 7 g sorghum flour 4.8 g honey 3.5 g soybean oil 0.3 g salt 8.9 g FCV-2 (flavonoid/caffeine/vitamin-mineral dry mix #2): 4 g cocoa powder, 3 g spinach powder; 1.5 g Moringa powder, 0.2 g onion powder, 1 g tomato powder; 0.2 g turmeric; 4 g green tea powder; +/−0.1 g vitamin/mineral powder 20 g protein mix 2 (13 g drained canned salmon; 1 g egg; 6 soy protein isolate)

1.7 ml DHA-rich fish oil fortified with fat soluble vitamins

Supplement

The additional vitamins and minerals needed to meet daily requirements are incorporated into the ingredient mix or provided in a separate multivitamin-mineral supplement as suitable for the population.

Instructions
  Ingredients are measured out and mixed together with sufficient water to form a dough, portioned out in individual servings, shaped into cookie round and then baked until cooked, approximately 14 minutes at 350 F.
  Biscuits are stored in clean container before consumption. The same recipe with adaptations well known to commercial food companies can be turned into a shelf-stable bar for mass production.
  Depending on whether the extra daily vitamins and minerals are incorporated into the biscuit or not the child will receive a multivitamin/mineral supplement to make up the remaining daily requirement values.

TABLE 4

| Constituent | Units | Total daily nutrient target | Daily intake from home food | Daily intake from supplement 1 (biscuit +/− vitamin) |
|---|---|---|---|---|
| Energy | kcal | 1242 | 942 | 297 |
| Protein | g | 30 | 16.8 | 13.5 |
| Protein from animal sources | g | 0 | 3 | |
| Fat | % energy | 30-60% | 6% | 55% |
| Carbohydrate | % energy | 20-50% | 86% | 32% |
| Fructose | % energy | <10% | — | <10% |
| Iron | mg | 11 | 2.8 | 8.2 |
| Magnesium | Mg | 250 | 128 | 94 |
| Phosphorous | Mg | 750 | 307 | 201 |
| Zinc | Mg | 16 | 3 | 13 |
| Vit C | Mg | 90 | 42 | 48 |
| Thiamine (B1) | Mg | 0.75 | 0.33 | 0.44 |
| Riboflavin (B2) | Mg | 0.99 | 0.18 | .81 |
| Niacin | Mg | 11 | 4 | 7 |
| Vit B6 | Mg | 0.99 | 0.50 | .49 |
| Vit B9 (folate) | Mg | 270 | 105 | 165 |
| Vit B12 | Mg | 1.2 | 0.2 | 1 |
| Vit A | RE, μg | 1190 | 19 | 1171 |
| Vit E | Mg | 14 | 1.0 | 13 |
| Vit D | Mg | 9 | 0 | 9 |
| Vit K | Mg | 55 | 8 | 47 |
| Vit B5 (pantothenic acid) | Mg | 3.5 | 2.6 | .9 |
| Vit B7 (biotin) | Mg | 12.5 | 0 | 12.5 |
| Choline* | Mg | 250 | 44 | 206 |
| Chromium* | Mg | 15 | 0 | 15 |
| Copper | Mg | 850 | 0 | 850 |
| Manganese | Mg | 1.5 | 2.7 | .5 |
| Selenium* | Mg | 30 | 30 | 9 |
| Molybdenum | Mg | 22 | 0 | 22 |
| Iodine | Mg | 90 | 0 | 90 |
| Omega-3 | G | 0.9 | 0.1 | .8 |
| EPA + DHA* | Mg | 300 | 0 | 558 |
| Caffeine* | Mg | 25-50 | N/A | 29.2 |
| Flavanoids* | Mg | 400 | N/A | 878 |
| Flavanols* | Mg | 250 | N/A | 614 |

Bold indicates higher target intake than currently recommended by international committees for malnutrition treatment/prevention.
Bold* indicates that current malnutrition treatment/prevention recommendations by USAID have no requirement value.
N/A data not available, anticipated very low values.
Electrolytes (sodium, potassium, chloride) included in recommended amounts.

5. Powdered Mixes to Supplement Home Food, for 5-Year Old Child

These mixes provides 1 individual daily supplement for all of active ingredients (flavonoids plus caffeine plus DHA/EPA), and are multiplied up as needed for number of children served. The 3 separate ingredient categories can be provided together, as in this example, or separately, depending on the anticipated shortfalls in home daily nutrients (See Tables 5 and 6 for nutritional information).
Composition of Powdered Mix with Supplementary Protein
  28.9 g FCV-3 (flavonoid/caffeine/vitamin-mineral dry mix #2): 4 g cocoa powder, 3 g spinach powder; 1.5 g Moringa powder, 0.2 g onion powder, 1 g tomato powder; 0.2 g turmeric; 4 g green tea powder; 0.1 g vitamin/mineral powder to complete daily recommended intakes; 3 g powdered salmon; 6 soy protein isolate
  1.7 g fish oil supplemented with fat-soluble vitamins to provide daily DHA/EPA need.
Instructions
  The dry mix and the fish oil mix are provided to families either in measured daily amounts per child or in a larger quantity with a measuring cup so that the family can measure out the required amount for each child.
  Mixes is added to home-prepared meal food to enrich it.

TABLE 5

| Constituent | Units | Total daily nutrient target | Daily intake from home food | Daily intake from Biscuit and Drink |
|---|---|---|---|---|
| Energy | kcal | 956 | 656 | 113 |
| Protein | G | 23 | 11.7 | 8.8 |
| Protein from animal sources | G | 0 | | 2.2 |
| Fat | % energy | 20-60% | 5% | 30% |
| Carbohydrate | % energy | 20-60% | 86% | 46% |
| Fructose | % energy | <10% | — | <10% |
| Iron | Mg | 9 | 2.0 | 7.0 |
| Magnesium | Mg | 190 | 90 | 100 |
| Phosphorous | Mg | 570 | 214 | 237 |
| Zinc | mg | 12 | 2 | 10 |
| Vit C | mg | 70 | 29 | 41 |
| Thiamine (B1) | mg | 0.575 | 0.23 | 1.1 |
| Riboflavin (B2) | mg | 0.77 | 0.13 | .64 |
| Niacin | mg | 8 | 3 | 5 |
| Vit B6 | mg | 0.77 | 0.34 | .40 |
| Vit B9 (folate) | μg | 210 | 73 | 137 |
| Vit B12 | μg | 0.77 | 0 | .47 |
| Vit A | RE, μg | 920 | 13 | 907 |
| Vit E | mg | 16.5 | 0.7 | 15.9 |
| Vit D | μg | 7 | 0 | 7 |
| Vit K | μg | 30 | 5 | 25 |
| Vit B5 (pantothenic acid) | mg | 3 | 2 | 1 |
| Vit B7 (biotin) | mg | 9.5 | 0 | 9.5 |
| Choline* | mg | 200 | 31 | 169 |
| Chromium* | μg | 11 | 0 | 11 |
| Copper | mg | 650 | 0 | 649 |
| Manganese | mg | 1.2 | 1.9 | .5 |
| Selenium* | μg | 20 | 21 | 9 |
| Molybdenum | μg | 17 | 0 | 17 |
| Iodine | μg | 90 | 0 | 90 |
| Omega-3 | g | 0.1-2.0 | 0.1 | 826 |
| EPA + DHA* | mg | 300-500 | 0 | 545 |
| Caffeine* | mg | 40 | N/A | 30.2 |
| Flavanoids* | mg | 20-2000 | N/A | 800 |
| Flavanols* | mg | 200-500 | N/A | 500 |

Composition of Powdered Mix without Supplementary Protein (Table 6)
  8.9 g FCV-3 (flavonoid/caffeine/vitamin-mineral dry mix #2): 4 g cocoa powder, 3 g spinach powder; 1.5 g Moringa powder, 0.2 g onion powder, 1 g tomato powder; 0.2 g turmeric; 4 g green tea powder; 0.1 g vitamin/mineral powder to complete daily recommended intakes
  1.7 g fish oil supplemented with fat-soluble vitamins to provide daily DHA/EPA need.
Instructions
  Ingredients are premixed and provided to families either in measured daily amounts per child or in a larger quantity with a measuring cup so that the family can measure out the required amount for each child.

Mix is added to home-prepared meal food to enrich it. For families where the home protein intake is anticipated to be adequate no additional instructions on protein consumption are provided. For families where there is a concern that protein intake is inadequate instructions are also given on how to add additional protein to the meal.

TABLE 6

| Constituent | Units | Total daily nutrient target | Daily intake from home food | Daily intake from Biscuit and Drink |
|---|---|---|---|---|
| Energy | kcal | 956 | 656 | 78 |
| Protein | g | 23 | 11.7 | 2.1 |
| Protein from animal sources | g | | 0 | 0 |
| Fat | % energy | 20-60% | 5% | 29% |
| Carbohydrate | % energy | 20-60% | 86% | 66% |
| Fructose | % energy | <10% | — | <10% |
| Iron | mg | 9 | 2.0 | 7.0 |
| Magnesium | mg | 190 | 90 | 100 |
| Phosphorous | mg | 570 | 214 | 237 |
| Zinc | mg | 12 | 2 | 10 |
| Vit C | mg | 70 | 29 | 41 |
| Thiamine (B1) | mg | 0.575 | 0.23 | 1.1 |
| Riboflavin (B2) | mg | 0.77 | 0.13 | .64 |
| Niacin | mg | 8 | 3 | 5 |
| Vit B6 | mg | 0.77 | 0.34 | .40 |
| Vit B9 (folate) | µg | 210 | 73 | 137 |
| Vit B12 | µg | 0.77 | 0 | .47 |
| Vit A | RE, µg | 920 | 13 | 907 |
| Vit E | mg | 16.5 | 0.7 | 15.9 |
| Vit D | µg | 7 | 0 | 7 |
| Vit K | µg | 30 | 5 | 25 |
| Vit B5 (pantothenic acid) | mg | 3 | 2 | 1 |
| Vit B7 (biotin) | mg | 9.5 | 0 | 9.5 |
| Choline* | mg | 200 | 31 | 169 |
| Chromium* | µg | 11 | 0 | 11 |
| Copper | mg | 650 | 0 | 649 |
| Manganese | mg | 1.2 | 1.9 | .5 |
| Selenium* | µg | 20 | 21 | 9 |
| Molybdenum | µg | 17 | 0 | 17 |
| Iodine | µg | 90 | 0 | 90 |
| Omega-3 | g | 0.1-2.0 | 0.1 | 826 |
| EPA + DHA* | mg | 300-500 | 0 | 545 |
| Caffeine* | mg | 40 | N/A | 30.2 |
| Flavanoids* | mg | 20-2000 | N/A | 800 |
| Flavanols* | mg | 200-500 | N/A | 500 |

6. Ready-to-Use-Therapeutic Food for 2-Year Old Child

This recipe makes 1 individual daily food requirement and is multiplied up as needed (See Table 7 for nutritional information).

Ingredients 20 g cashew butter 10 g dextrose 4 g soybean oil 11.6 g FCV-4 (flavonoid/caffeine/vitamin-mineral dry mix #4): 4 g cocoa powder, 7 g spinach powder; 0.15 g vitamin/mineral powder)

4.5 g protein mix 2 (4.5 g whey)

1.9 ml DHA-rich fish oil

This is a ready-to-use formulation that is prepared commercially and packaged for individual daily use using appropriately safe ingredients and safe quality control measures.

TABLE 7

| Constituent | Units | WHO recommendations for RUTF for SAM (per 100 g product) | Supplement composition |
|---|---|---|---|
| Energy | kcal | 520-550 | 520 |
| Protein | g | 10-12% energy | 12% |
| Protein from animal sources | % energy | 50% | 50% |
| Fat | % energy | 45-60% | 58% |
| Carbohydrate | % energy | — | 37% |
| Fructose | w/w % | — | <10% |
| Iron | mg | 10-14 | same |
| Magnesium | mg | 80-140 | same |
| Phosphorous | mg | 300-600 | same |
| Zinc | mg | 11-14 | same |
| Vit C | mg | 50 | same |
| Thiamine (B1) | mg | 0.5 | same |
| Riboflavin (B2) | mg | 1.6 | same |
| Niacin | mg | 5 | same |
| Vit B6 | mg | 0.6 | same |
| Vit B9 (folate) | µg | 200 | same |
| Vit B12 | µg | 1.6 | same |
| Vit A | mg | 0.8-1.1 | Same |
| Vit E | mg | 20 | same |
| Vit D | µg | 15-20 | same |
| Vit K | µg | 15-30 | same |
| Vit B5 (pantothenic acid) | mg | 3 | same |
| Vit B7 (biotin) | µg | 60 | same |
| Choline* | mg | — | 200 |
| Chromium* | µg | — | 11 |
| Copper | mg | 1.4-1.8 | same |
| Manganese* | mg | — | 1.2 |
| Selenium* | µg | 20-40 | same |
| Molybdenum* | µg | — | 17 |
| Iodine | µg | 70-140 | same |
| Omega-3 | g | 0.2-2.5% energy | 2.5% |
| EPA + DHA* | mg | — | 60-150 mg/kg |
| Caffeine* | mg | — | 5 mg |
| Flavanoids* | mg | — | 875 mg |
| Flavanols* | mg | — | 500 mg |

Bold* indicates that current malnutrition treatment/prevention recommendations by USAID have no requirement value.
Electrolytes (sodium, potassium, chloride) included in recommended amounts.

7. Therapeutic Food for Home or Clinic Preparation for 2-Year Old Child

This recipe makes 1 individual daily food requirement and is multiplied up as needed (See Table 8 for nutritional information).

Ingredients 48.5 g FCV-6 (flavonoid/caffeine/vitamin-mineral mix #6): 4.4 g cocoa powder, 5.3 g spinach powder; 2.4 g green tea powder; 0.1 g vitamin/mineral powder; 5 g fish protein; 2 g soy protein isolate, 10 g rice flour; 4 g dextrose, 13.4 g soybean oil, 1.9 ml DHA-rich oil fortified with fat soluble vitamins This formulation is prepared by mixing the package of ingredients with sterile water and boiling and cooling to make a lukewarm gruel for use.

TABLE 8

| Constituent | Units | WHO recommendations for RUTF for SAM (per 100 g product) | Supplement composition |
|---|---|---|---|
| Energy | kcal | 520-550 | 520 |
| Protein | g | 10-12% energy | 11.8% |

TABLE 8-continued

| Constituent | Units | WHO recommendations for RUTF for SAM (per 100 g product) | Supplement composition |
|---|---|---|---|
| Protein from animal sources | % energy | 50% | 50% |
| Fat | % energy | 45-60% | 60% |
| Carbohydrate | % energy | — | 30% |
| Fructose | w/w % | — | 9.4% |
| Iron | mg | 10-14 | same |
| Magnesium | mg | 80-140 | same |
| Phosphorous | mg | 300-600 | same |
| Zinc | mg | 11-14 | same |
| Vit C | mg | 50 | same |
| Thiamine (B1) | mg | 0.5 | same |
| Riboflavin (B2) | mg | 1.6 | same |
| Niacin | mg | 5 | same |
| Vit B6 | mg | 0.6 | same |
| Vit B9 (folate) | µg | 200 | same |
| Vit B12 | µg | 1.6 | same |
| Vit A | mg | 0.8-1.1 | same |
| Vit E | mg | 20 | same |
| Vit D | µg | 15-20 | same |
| Vit K | µg | 15-30 | same |
| Vit B5 (pantothenic acid) | mg | 3 | same |
| Vit B7 (biotin) | µg | 60 | same |
| Choline* | mg | — | 200 |
| Chromium* | µg | — | 11 |
| Copper | mg | 1.4-1.8 | same |
| Manganese* | mg | — | 1.2 |
| Selenium* | µg | 20-40 | same |
| Molybdenum* | µg | — | 17 |
| Iodine | µg | 70-140 | same |
| Omega-3 | g | 0.2-2.5% energy | 2.5% |
| EPA + DHA* | mg | — | 545 mg |
| Caffeine* | mg | — | 20 mg |
| Flavanoids* | mg | — | 850 mg |
| Flavanols* | mg | — | 540 mg |

Bold* indicates that current malnutrition treatment/prevention recommendations by USAID have no requirement value.
Electrolytes (sodium, potassium, chloride) included in recommended amounts.

Example 4

Clinical Study Results
Methods
Study Location and Participants

Guinea-Bissau is a small low-income country in West Africa with a population of 1.7 million. Families living in rural villages grow most of the food they eat, including rice (the staple food), millet, corn, sorghum, groundnuts, cassava, sweet potatoes, mangoes, and domestic animals. In addition, they catch wild foods including fish and small mammals, and grow cashews to sell for additional rice and other popular foods including sugar, oil and bread. The study was conducted in 2 villages in the Oio district of Guinea-Bissau, which is one of the poorest regions of the country and has very high rates of stunting and moderate-acute malnutrition (MAM) (Batra P, Schlossman N, Balan I, Pruzensky W, Balan A, Brown C, Gamache M G, Schleicher M M, de Sa A B, Saltzman E, Wood L, Roberts S B. A Randomized Controlled Trial Offering Higher-Compared with Lower-Dairy Second Meals Daily in Preschools in Guinea-Bissau Demonstrates an Attendance-Dependent Increase in Weight Gain for Both Meal Types and an Increase in Mid-Upper Arm Circumference for the Higher-Dairy Meal. The Journal of nutrition. 2016; 146(1):124-32). The villages were a convenience sample that were comparable in terms of number of inhabitants, ethnicity, religion and interest in study participation, and were also sufficiently large to make study recruitment feasible. Inclusion criteria were: parents willing to have their child participate, and the child was reported to be 2-3 years (20 per village) or 6-7 years (20 per village). An additional inclusion criterion for the older age group was that the child was enrolled in 1st grade in the village elementary school. Exclusion criteria were: the child had one or more food allergies, he or she would not be in the village for the duration of the study, or had severe acute malnutrition (SAM) as indicated by a mid-upper arm circumference (MUAC) in the red zone of a tape measure.

Institutional Review Board (IRB) permission to conduct the study was provided by the ethical committee of the government of Guinea-Bissau. In addition, Tufts University provided permission for all measurements except near infrared spectroscopy (NIRS). The NIRS sub study was approved by Guinea-Bissau and Massachusetts General Hospital IRBs. A post-hoc agreement was implemented to share deidentified data between the two U.S. institutions. Following an explanation of the study protocol, all mothers or legal guardians of children agreed to participation, and provided their informed consent with a signature or thumbprint in the presence of a member of the research team and a community health worker. Participating families received an allotment of rice to thank them for participation.

Study Protocol

This 11-week pilot study was a village-randomized controlled study comparing randomization to receive a new locally-prepared supplement with randomization to an assessment-only control in 2 villages. Two age groups, 2-3 and 6-7 years, were enrolled based on parent-reported age. The supplement was provided 5 days per week for 11 weeks to intervention children. The primary outcome was two assessments of children's executive function abilities (working memory, reverse categorization), and secondary outcomes included growth, hemoglobin, and skin carotenoids. In addition, an index of cerebral blood flow (CBFi) and an index of tissue absorption (µai) was measured at 12 weeks with a near infrared spectroscopy (NIRS) method called diffuse correlation spectroscopy (DCS) McGovern-Dole. The Global Effort to Reduce Child Hunger and Increase School Attendance Report to the United States Congress, Fiscal Years 2012-2014. 216 June 2016. Report No. 16. Specialized nutritious foods, (2016)) to evaluate NIRS as a method potentially suitable for assessment of cognitive function in large population studies.

Baseline assessments included demographic information, cognitive variables, anthropometry (weight, height, head circumference and MUAC), and skin carotenoids in all children. After baseline, villages were assigned a number and their treatment (intervention or control) was based on a randomization schema generated in SAS. The villagers randomized to the intervention group received the new supplement at the community health center 5 mornings per week. Community health center workers distributed the supplement and tracked supplement attendance and consumption after training by the research staff from the International Partnership for Human Development and the U.S. team. When a child's caregiver was routinely someone other than the mother, that person was allowed to bring the child for supplement distribution. Outcome assessments obtained at baseline were repeated at the end of the study period before the supplement distribution was completed. In addition, measurements of CBFi and tissue absorption with NIRS-DCS were done at the end of the study.

The Supplementary Food

The supplement formulation used in this study was designed as a substitute for typical ready to use supplementary foods (RUSFs) and fortified blended foods (FBFs), which are used in a variety of ways in low-income countries including in supplementary feeding programs for mothers and children to prevent growth faltering, for community treatment of MAM, and for school feeding programs. In addition to the nutrients defined by WHO for nutrient and micronutrient content of RUSF and FBF, the new supplement formulation included the following ingredients (See formulations in Examples 2-3): choline (Zeisel S H, da Costa K A. Choline: an essential nutrient for public health. Nutrition reviews. 2009; 67(11):615-23. Epub 2009/11/13); fish oil containing the essential omega-3 polyunsaturated fatty acids eicosapentaenoic acid (EPA) and docosahexaenoic acid (DHA) (Dyall S C. Long-chain omega-3 fatty acids and the brain: a review of the independent and shared effects of EPA, DPA and DHA. Frontiers in aging neuroscience. 2015; 7:52. Epub 2015/05/09); two additional micronutrients (molybdenum, chromium) that are not specifically related to cognition but are now defined as essential nutrients in U.S. national requirements for healthy children (da Costa K A, Gaffney C E, Fischer L M, Zeisel S H. Choline deficiency in mice and humans is associated with increased plasma homocysteine concentration after a methionine load. The American journal of clinical nutrition. 2005; 81(2):440-4. Epub 2005/02/09); high-flavanol sources of cocoa and green tea (Nehlig A. The neuroprotective effects of cocoa flavanol and its influence on cognitive performance. British journal of clinical pharmacology. 2013; 75(3):716-27. Epub 2012/07/11); higher levels of Vitamin K than WHO recommendations (Ferland G. Vitamin K and the nervous system: an overview of its actions. Advances in nutrition (Bethesda, Md). 2012; 3(2):204-12. Epub 2012/04/21); and lower levels of calcium to facilitate iron absorption, taking into consideration both the negative effect of high levels of calcium on non-heme iron absorption and the potential for added polyphenols to reduce absorption (Abbaspour N, Hurrell R, Kelishadi R. Review on iron and its importance for human health. Journal of research in medical sciences: the official journal of Isfahan University of Medical Sciences. 2014; 19(2):164-74. Epub 2014/04/30).

The new supplement goals were combined with projected home food consumption to calculate supplement nutrients as those missing in the home diet. Due to practical considerations, the supplementary nutrients were delivered in a combination of a locally prepared biscuit and chewable micronutrient gummies (Children's MV-Alive, Nature's Way Products LLC, WI; Vitamin Friend's Iron, Vitamin Friends LLC, CA) but future use of the formulation could include combinations of the ingredients and nutrients into a single mix or ready-to-use product. The biscuit was prepared from a combination of the mix of new ingredients together with locally sourced ingredients (peanuts, oil, honey, sugar, eggs and moringa). Village bakers were trained by the research staff to prepare the biscuits, keep records of production and deliver the baked goods to community health centers for distribution. Community health workers distributed the supplement in the morning, made records of attendance and monitored consumption levels.

Cognitive Assessments

The cognitive assessments included two measures of executive functioning in early childhood: working memory and task switching abilities. Specific tasks were chosen based on their potential to be culturally adapted for the local villages, to be reliably conducted by the local research team, to require minimal instructions to the children, and to fit within a 15-minute testing timeframe (given the expected time needed for the additional measures and the expected attentiveness of a typical child). The assessments were administered in a quiet room in the local village by a member of the local research team who had been trained by the senior researcher who designed the tests (PM). Children could participate alone or could sit on the knee of their mother or a caregiver, as they preferred. Any adults present were seated behind the child, not told of the specific behaviors or measures of interest for each task, and were instructed to not help or provide answers to the child. If a child became fussy or upset, the individual task or entire assessment was stopped; and caregivers were also instructed that they could stop the assessments at any time. All sessions were video-recorded for later coding by coders unaware of participant randomization. Sessions were also reviewed by experienced test administrators for protocol adherence.

Working memory was assessed in both young and older children with the Spin the Pots task (Hughes & Ensor, 2005; age modifications guided by Hostinar et al, 2012). Children were presented with an array of small opaque cups, each covered by a lid with a distinct color and/or pattern, all placed upon a circular base platform. At the start of the task, children were shown that the lids could be removed and that stickers could be hidden inside each cup. The test administrator hid stickers in a subset of the total number of cups (young children: 4 of 6 total cups; older children: 8 of 12 total cups) and then covered the entire array with an opaque cover. The test administrator then lifted the cover and allowed the child to search for a sticker. If the child found a sticker, the child could keep the sticker; if they did not find a sticker, the test administrator let the child see the bottom of the empty cup and told them there was not a sticker there. The circular base was then covered and rotated 180°. The cover was then removed and the child was allowed to search again. This procedure continued until the child found all the hidden stickers or until they reached a predetermined set of trials (young children: 12 trials; older children: 18 trials). Children's performance was assessed by the total number of stickers found as well as a categorical assessment of whether children found all of the hidden stickers.

Task-switching was assessed through a Reverse Categorization task modeled after Carlson, Mandell, and Williams (2004). For the 2-year-old children, children were presented with a basket full of animals and told that the basket included both 'mommy' animals and 'baby' animals. They were then shown two boxes: one box had an image of an adult animal on the front of the box and the other box had an image of a baby animal on the front of the box. The test administrator directed the child's attention to the front of the boxes and labeled them the "Mommy" and "Baby" boxes. The test administrator then told the child they were going to play a game in which they put 'baby' animals in the 'baby' box and 'mommy' animals in the 'mommy' box. The test administrator then demonstrated accurate sorting with 6 animals (3 mommy, 3 baby) during a pre-switch phase. He instructed the child, "This is a [baby/mommy] animal, so it goes in the [baby/mommy] box." The child was then allowed to sort the next 6 animals (3 mommy, 3 baby). For each animal, the test administrator labeled the animal ('baby' vs. 'mommy') and asked the child where the animal went. Children were praised for accurate sorting or corrected with a restatement of the rule, for each of the 6 trials. Children were next told that they were now going to play a "silly game" in which they put all the 'mommy' animals in the 'baby' box and all of the 'baby' animals' in the 'mommy' box. During this post-switch phase, children were then allowed to sort 12 additional animals (6 mommy, 6 baby). The experimenter labeled the size and restated the rule for each animal; however, they did not correct inaccurate sorting. The procedure was similar for the 6-year-old children, with the following exceptions. During the pre-switch phase, the test administrator labeled the size of only the first two animals (e.g., mommy cow), subsequently only labeling the kind of animal (e.g., cow) for the remaining 4 animals. During the post-switch phase, the test administrator labeled only the kind, but not the size of the animal. He also only reminded the children of the rule on 1st and 7th trial. Similar to the 2-year-old children, 6-year-old children were corrected for errors during the pre-switch, but not the post-switch phases. The total number of accurate sorts during the post-study phase was recorded.

Two additional cognitive assessments were also conducted. An object-directed manual exploration task, which was conducted only in 2-year-old children, was designed to assess children's rate of habituation and novelty preferences and involved free play with a series of small animal toys. A delay of gratification test, which was conducted only in the 6-year-old children, involved measuring how long children could wait to play with a novel set of toy cars and roller-coaster.

Anthropometric and Biochemical Assessments

Outcome assessments were performed by a group of trained medical/nursing staff seconded from the Guinea-Bissau Ministry of Health who had no role in study design or supplement distribution. Anthropometric assessments were made in both the children and their mother or usual caregiver. Non-fasting weight was measured at baseline and 11 weeks using a digital calibrated scale weighing to ±0.1 kg (floor scale model 813, Seca, Chino, CA). Height was assessed using an upright stadiometer measuring to 0.1 cm for (model 213, Seca).

Mid-upper arm circumference (MUAC) was taken at the midpoint between the acromion process of scapula and olecranon process with a paper tape using standardized methods. Hemoglobin was measured in duplicate by pulse co-oximetry, a non-invasive technique validated for anemia screening (Hsu D P, French A J, Madson S L, Palmer J M, Gidvani-Diaz V. Evaluation of a Noninvasive Hemoglobin Measurement Device to Screen for Anemia in Infancy. Maternal and child health journal. 2016; 20(4):827-32. Epub 2015/12/26) which uses a multiple wavelength spectrophotometric sensor situated in a comfortable finger clip (Pronto-7, Masimo Corp, Irving CA). Due to technical challenges in the field, the hemoglobin measurements could not be collected at baseline, so only 11-week data are available.

Skin carotenoid content was measured in duplicate in the palm of each hand by Resonance Raman Spectroscopy (Hata T R, Scholz T A, Ermakov I V, McClane R W, Khachik F, Gellermann W, Pershing L K. Non-invasive raman spectroscopic detection of carotenoids in human skin. The Journal of investigative dermatology. 2000; 115(3):441-8. Epub 2000/08/22; Ermakov I V, Ermakova M R, Gellermann W, Lademann Jr. Noninvasive selective detection of lycopene and β-carotene in human skin using Raman spectroscopy. BIOMEDO. 2004; 9(2):332-8), to provide an index of diet quality that could potentially also serve as an independent marker of supplement adherence (since the supplement contained carotenoids). Measurements were made in the palm of the hand because the carotenoid concentration is high and differences in pigmentation among various skin types are minimal at this location, and the stratum corneum thickness of the palm (~400 mm) is high compared with other skin sites. Measurements were made with a NuSkin scanner (Pharmanex Global Research, UT), which uses a laser power of <10 mW and an exposure time of 30 seconds per measurement with an elliptical spot size of 2 mm by 3 mm.

Cerebral Blood Flow by Near Infrared Spectroscopy

DCS was used to assess cerebral hemodynamics. DCS, like NIRS, use near-infrared light, but in addition to quantifying tissue absorption ($\mu_a$i) by measuring light attenuation at 785 nm, it also quantify an index of blood flow (CBFi) by measuring the temporal fluctuations of the light speckle pattern generated by the dynamic scattering of red blood cells (Bogale A, Stoecker B J, Kennedy T, Hubbs-Tait L, Thomas D, Abebe Y, Hambidge K M. Nutritional status and cognitive performance of mother-child pairs in Sidama, Southern Ethiopia. Maternal & child nutrition. 2013; 9(2): 274-84. Epub 2011/08/03). Numerous studies in humans and in animals have shown that CBFi agree very well with CBF values measured with gold standard methods (Sudfeld C R, McCoy D C, Fink G, Muhihi A, Bellinger D C, Masanja H, Smith E R, Danaei G, Ezzati M, Fawzi W W. Malnutrition and Its Determinants Are Associated with Suboptimal Cognitive, Communication, and Motor Development in Tanzanian Children. The Journal of nutrition. 2015; 145(12):2705-14. Epub 2015/10/09; Mendez M A, Adair L S. Severity and timing of stunting in the first two years of life affect performance on cognitive tests in late childhood. The Journal of nutrition. 1999; 129(8):1555-62. Epub 1999/07/27). By simultaneously measuring both SO2 and CBFi in previous studies in infants, it was shown that CBFi is more tightly correlated with cerebral oxygen metabolism than cerebral hemoglobin oxygenation (SO2) (Grantham-McGregor S, Ani C. A review of studies on the effect of iron deficiency on cognitive development in children. The Journal of nutrition. 2001; 131(2s-2):649S-66S; discussion 66S-68S. Epub 2001/02/13), typically measured with NIRS and is a superior indicator of brain development (Prado E L, Dewey K G. Nutrition and brain development in early life. Nutrition reviews. 2014; 72(4):267-84. Epub 2014/04/02; Husaini M A, Karyadi L, Husaini Y K, Sandjaja, Karyadi D, Pollitt E. developmental effects of short-term supplementary feeding in nutritionally-at-risk Indonesian infants. The American journal of clinical nutrition. 1991; 54(5):799-804) and brain health (Pollitt E, Watkins W E, Husaini M A. Three-month nutritional supplementation in Indonesian infants and toddlers benefits memory function 8 y later. The American journal of clinical nutrition. 1997; 66(6):1357-63. Epub 1997/12/12) compared to SO2.

For this study, a custom DCS device built at the Martinos Center at MGH was used. The system includes 4 photon counting detectors, one long coherence length laser at 785 nm, and a FPGA based software correlator. Custom fiber optics monitors were used to measure the children enrolled in the study. The light power at the probe was around 20 mW and diffused over a 5 mm diameter spot. This was well under ANSI standards limits for laser light exposure. Light was detected at 0.5, 1.5, 2 and 2.5 cm separation distance from the source. Because of the low light level at the largest distance, only the first three separations (0.5, 1.5 and 2.0 cm) where used to calculate $\mu_a$i (Nahar B, Hossain M I, Hamadani J D, Ahmed T, Huda S N, Grantham-McGregor S M, Persson L A. Effects of a community-based approach of food and psychosocial stimulation on growth and development of severely malnourished children in Bangladesh: a randomized trial. European journal of clinical nutrition. 2012; 66(6):701-9) and discriminate extracerebral (scalp BFi, calculated at 0.5 cm source-detector separation) from cerebral blood flow (CBFi at 2 cm source-detector separation) (Calder P C. Omega-3 fatty acids and inflammatory processes. Nutrients. 2010; 2(3):355-74. Epub 2010/03/01). A scattering coefficient of 5 cm-1 was assumed in all groups to calculate CBFi and μai (34). Measurements consisted of positioning the optical monitor in the upper forehead of the subject and keeping it in place by hand for 20 seconds during data recording. Measurements were acquired in the left and right forehead, and if the child moved or the detected light signal was low, measurements were repeated one more time. No pressure was applied to the monitor, which was sanitized between subjects.

Data Analyses

Subjects with missing or implausible values were excluded from analyses. The ages of enrolling participants were based on parental reporting at baseline, and when checked against birth certificates at the end of the study some were found to be outside the original planned age range. These data were retained in analyses with IRB permission. Z-scores for weight-for-age (WAZ), height-for-age (HAZ) and weight-for-height (WHZ) were calculated with macros based on WHO child growth standards (Kuratko C N, Barrett E C, Nelson E B, Salem N, Jr. The relationship of docosahexaenoic acid (DHA) with learning and behavior in healthy children: a review. Nutrients. 2013; 5(7):2777-810. Epub 2013/07/24). All analyses were stratified by age group (young and older categories). Differences in baseline variables between the two supplement groups and control group were compared using chi-squared ($\chi 2$) for categorical variables, one-way ANOVA for continuous variables and the Krusal-Wallis test for non-normal continuous variables. Primary analyses were intention-to-treat (ITT) based on the initial study group randomization. In addition, ANCOVA models were performed with age as a covariate to adjust for any imbalance due to randomization at the village level and also to reduce any underlying variability attributable to these variables. Analyses were performed using SAS version 9.3 (SAS Institute, Inc., North Carolina), and statistical significance for all variables was set at a 2-sided P of 0.05.

Results

Baseline and change data for child anthropometry and skin carotenoid content, and hemoglobin at 11 weeks, are shown in Table 9. There were no significant differences between groups for any of the baseline variables, and both groups of children were undernourished as seen by negative mean z-scores for all anthropometric variables. Mean values for z-scores tended to be somewhat worse in the intervention group. Changes in anthropometry over the 11-week study and hemoglobin at 11 weeks are also shown in Table 9. Although mean changes were slightly more beneficial for all variables in the intervention group versus the control, there were no significant differences in changes over time for any of these variables in either age-group. It should be noted emphasized that the study was a pilot, and was substantially underpowered to detect significant differences between groups.

Table 10 summarizes the cognitive data both age groups. Results show that, for the younger age group, randomization to the supplemented group was associated with positive effects on children's working memory. In the Spin the Pots task, younger children in the intervention group found more stickers (mean=3.44) and tended to be more likely to find all the stickers than children in the control group. The task-switching test is not reported for younger children due to lower numbers completing the test. For the 6-year-old children, randomization to the intervention group was not significantly associated with children's working memory or task switching abilities; however, raw scores were high in both conditions for the Spin the Pots task.

To test the utility of CBFi measurements to assess brain cognitive abilities in children at risk of malnutrition, data analysis combining the intervention and control children was performed. Mean values for CBFi at 2 cm in in the younger and older groups were 0.18±0.01 and 0.20±0.01, respectively. Mean values for absorption (μa @785 nm) in in the younger and older groups were 10.4±0.05 and 11.0±0.06, respectively. There was a statistically significant correlation between animal sorted correctly and CBFi in the right frontal region in six years old (R=0.44, P=0.038). This correlation is illustrated in FIG. 1 along with depiction of village measurements. Some anthropometric measures correlated with CBFi in 2 or 6 years old groups. In particular, in six years old CBFi in the right frontal region it was negatively correlated with arterial oxygenation (−0.45, P=0.034) and head circumference (R=−0.51, P=0.016). Two years old CBFi was negatively correlated with HAZ (right CBFi R=−0.43, P=0.001; left CBFi R=−0.49, P=0.004). Tissue absorption didn't correlate with any anthropometric measure.

In summary, stunting and MAM remain widespread worldwide, and current food products designed to prevent and treat these conditions do not reverse the cognitive damage associated with undernutrition in childhood.

TABLE 9

|  | Intervention | | | Control | | | P-value * |
| --- | --- | --- | --- | --- | --- | --- | --- |
|  | Baseline | 11 weeks | Δ | Baseline | 11 weeks | Δ |  |
| 2 Years |  |  |  |  |  |  |  |
| n | 20 | 18 | 18 | 18 | 17 | 17 |  |
| Age, years | 2.4 ± 0.4 |  |  | 2.2 ± 0.0.4 |  |  | 0.1166 |
| WAZ | −1.43 ± 0.94 | −1.30 ± 0.99 | 0.01 ± 0.35 | −1.20 ± 0.87 | −1.27 ± 0.86 | −0.07 ± 0.30 | 0.3860 |
| HAZ | −2.08 ± 1.37 | −2.03 ± 1.04 | 0.04 ± 0.70 | −1.80 ± 0.87 | −1.89 ± 0.81 | −0.07 ± 0.30 | 0.7952 |
| WHZ | −0.36 ± 0.81 | −1.30 ± 0.99 | −0.02 ± 0.61 | −0.29 ± 0.69 | −0.29 ± 0.77 | −0.03 ± 0.55 | 0.6305 |
| Arm circumference, cm | 14.93 ± 1.12 | 15.05 ± 1.11 | 0.13 ± 0.67 | 14.81 ± 1.14 | 15.09 ± 1.07 | 0.20 ± 0.48 | 0.7167 |
| Head circumference, cm | 47.04 ± 1.73 | 47.59 ± 1.53 | 0.35 ± 1.25 | 47.52 ± 1.94 | 47.46 ± 1.83 | −0.03 ± 0.79 | 0.2645 |

TABLE 9-continued

|  | Intervention | | | Control | | | P-value * |
| --- | --- | --- | --- | --- | --- | --- | --- |
|  | Baseline | 11 weeks | Δ | Baseline | 11 weeks | Δ |  |
| Hemoglobin, g/dL |  | 12.29 ± 0.92 |  |  | 11.96 ± 0.72 |  | 0.251 |
| Skin carotenoid content, Raman counts × 10³ | 24.6 ± 7.2 (n = 15) | 30.7 ± 8.9 (n = 15) | 6.1 ± 8.4 (n = 15) | 34.8 ± 6.7 (n = 15) | 38.1 ± 10.6 (n = 14) | 3.4 ± 12.4 (n = 14) | 0.498 |
| 6 Years |  |  |  |  |  |  |  |
| n | 20 | 19 | 19 | 20 | 20 | 20 |  |
| Age, years | 5.9 ± 0.3 |  |  | 6.1 ± 0.6 |  |  | 0.095 |
| WAZ | −1.78 ± 0.92 | −1.77 ± 0.94 | 0.05 ± 0.24 | −1.28 ± 1.35 | −1.23 ± 1.05 | 0.05 ± 0.31 | 0.7390 |
| HAZ | −1.74 ± 0.99 | −1.72 ± 0.95 | 0.05 ± 0.13 | −1.13 ± 0.99 | −1.11 ± 1.31 | 0.02 ± 0.10 | 0.4380 |
| BMI z-score | −0.96 ± 0.84 | −0.94 ± 0.80 | 0.02 ± 0.46 (n = 19) | −0.79 ± 0.76 | −0.74 ± 0.65 | 0.05 ± 0.48 | 0.6027 |
| Arm circumference, cm | 15.44 ± 1.30 | 15.30 ± 1.11 | −0.15 ± 0.57 | 15.78 ± 0.84 | 16.02 ± 0.92 | 0.24 ± 0.57 | 0.0767 |
| Head circumference, cm | 50.0 ± 1.38 (n = 17) | 49.58 ± 1.42 (n = 20) | −0.35 ± 0.74 (n = 17) | 50.13 ± 1.47 (n = 19) | 49.86 ± 1.56 (n = 19) | −0.20 ± 0.77 (n = 19) | 0.6351 |
| Hemoglobin, g/dL |  | 12.45 ± 0.87 |  |  | 12.49 ± 0.63 |  | 0.882 |
| Skin carotenoid content, Raman counts × 10³ | 32.6 ± 12.1 | 35.8 ± 9.1 | 3.2 ± 10.2 | 37.4 ± 8.0 | 39.8 ± 8.4 | 2.4 ± 9.1 | 0.784 |

TABLE 10

|  | Intervention | Control | P-value * |
| --- | --- | --- | --- |
| 1-3 Years |  |  |  |
| n | 16 | 16 |  |
| Baseline age, years | 2.49 ± 0.40 | 2.23 ± 0.38 |  |
| WAZ | −1.26 ± 1.03 | −1.25 ± 0.84 (n = 15) | 0.1526 |
| HAZ | −2.01 ± 1.11 | −1.85 ± 0.85 (n = 15) | 0.6707 |
| WHZ | −0.19 ± 0.92 | −0.31 ± 0.75 (n = 15) | 0.1272 |
| Cognition |  |  |  |
| # Stickers Found | 3.44 ± 0.63 | 2.88 ± 0.62 | 0.0435*** |
| % Found All Stickers | 50.0% | 12.5% | 0.076** |
| 5-7 Years |  |  |  |
| n | 20 | 20 |  |
| Baseline age, years | 5.87 ± 0.28 | 6.11 ± 0.55 |  |
| WAZ | −1.78 ± 0.92 | −1.28 ± 0.99 | 0.7390 |
| HAZ | −1.74 ± 0.99 | −1.13 ± 1.35 | 0.4380 |
| BMI z-score | −0.96 ± 0.84 (n = 19) | −0.79 ± 0.76 | 0.6027 |
| Cognition |  |  |  |
| # Stickers Found | 6.60 ± 0.99 | 7.05 ± 0.83 | 0.0755*** |
| % Found All Stickers | 25.0% | 30% | 0.5384** |
| % Correctly Sorted Animals | 8.90 ± 2.99 | 9.40 ± 2.89 | 0.7809*** |

Example 4

Formulations

This example describes an additional formulation. Tables 11-14 provide components of bulk and single serving products. Formulations are administered and assessed for functionality as described in Example 3 above.

TABLE 11

|  |  | 2 year olds | | 6 year olds | |
| --- | --- | --- | --- | --- | --- |
|  |  | Single Bag (28 Cookies) | Single Cookie | Single Bag (24 Cookies) | Single Cookie |
| Baggie mix (g) | Cacoa powder | 170.24 | 6.08 | 175.2 | 7.30 |
|  | Moringa | 11.76 | 0.42 | 12 | 0.50 |
|  | Matcha | 23.24 | 0.83 | 24 | 1.00 |
|  | Soy protein | 210 | 7.50 | 216 | 9.00 |
|  | Whey protein | 120.4 | 4.30 | 124.8 | 5.20 |
|  | Cinnamon | 2.24 | 0.08 | 2.4 | 0.10 |
|  | Iodized salt | 3.5 | 0.13 | 3.6 | 0.15 |
|  | Honey | 224 | 8.00 | 228 | 9.50 |
|  | Omega 3 fish oil | 39.76 | 1.42 | 41.04 | 1.71 |
|  | Peanut butter | 386.4 | 13.80 | 396 | 16.50 |
|  | Vegetable oil | 163.24 | 5.83 | 168 | 7.00 |
|  | Sugar | 98 | 3.50 | 100.8 | 4.20 |

TABLE 11-continued

|  |  | 2 year olds | | 6 year olds | |
| --- | --- | --- | --- | --- | --- |
|  |  | Single Bag (28 Cookies) | Single Cookie | Single Bag (24 Cookies) | Single Cookie |
| Vitamins, pure (g) | Flintstone, ground | 31.92 | 1.14 | 27.36 | 1.14 |
|  | Beta Carotene | 0.005046252 | 0.000180223 |  |  |
|  | Vitamin C | 2.62304112 | 0.09368004 | 2.25325 | 0.09389 |
|  | Vitamin D | 0.00013104 | 0.00000468 | 0.00010 | 0.000004 |
|  | Vitamin E | 0.309703324 | 0.011060833 | 0.25452 | 0.011 |
|  | Vitamin K | 4.245E−05 | 1.51607E−06 | 0.00095 | 0.00004 |
|  | Niacin | 0.242222798 | 0.008650814 | 0.08039 | 0.003 |
|  | Vitamin B6 | 0.003301091 | 0.000117896 | 0.00320 | 0.0001 |
|  | Choline | 1.06927296 | 0.03818832 | 0.53108 | 0.022 |
|  | Chromium | 0.00000042 | 0.000000015 | 0.00000 | 0.000000002 |
|  | Iodine | 0.000924 | 0.000033 | 0.00079 | 0.000033 |
|  | Magnesium | 0.4929414 | 0.01760505 |  |  |
|  | Manganese | 0.042850293 | 0.001530368 | 0.03670 | 0.00153 |
|  | Molybedenunn | 0.00063112 | 0.00002254 | 0.00054 | 0.0000225 |
|  | Selenium | 0.00107674 | 3.8455E−05 |  |  |
|  | Zinc | 0.083076504 | 0.002967018 | 0.08015 | 0.003339 |

TABLE 12

|  |  | 2 year olds | | 6 year olds | |
| --- | --- | --- | --- | --- | --- |
|  |  | Single Bag (28 Cookies) | Single Cookie | Single Bag (24 Cookies) | Single Cookie |
| Vitamins, purchased form (g) | Flintstone, ground | 31.920000 | 1.140000 | 27.360000 | 1.140000 |
|  | Beta Carotene | 6.055503 | 0.216268 |  |  |
|  | Vitamin C | 2.520000 | 0.090000 | 2.160000 | 0.090000 |
|  | Vitamin D | 0.048533 | 0.001733 | 0.038005 | 0.001584 |
|  | Vitamin E | 0.263508 | 0.009411 | 0.225864 | 0.009411 |
|  | Vitamin K | 0.000866 | 0.000031 | 0.019436 | 0.000810 |
|  | Niacin | 0.242223 | 0.008651 | 0.080390 | 0.003350 |
|  | Vitamin B6 | 0.003301 | 0.000118 | 0.003198 | 0.000133 |
|  | Choline | 2.673182 | 0.095471 | 1.327693 | 0.055321 |
|  | Chromium | 0.000017 | 0.0000006 | 0.000014 | 0.0000006 |
|  | Iodine | 0.001221 | 0.000044 | 0.001046 | 0.000044 |
|  | Magnesium | 3.286276 | 0.117367 |  |  |
|  | Manganese | 0.389225 | 0.013901 | 0.333621 | 0.013901 |
|  | Molybedenunn | 0.025245 | 0.000902 | 0.021638 | 0.000902 |
|  | Selenium | 0.107674 | 0.003845 |  |  |
|  | Zinc | 0.106508 | 0.003803869 | 0.102754 | 0.004281 |

TABLE 13

|  |  | 2.9-4.15 year olds | |
| --- | --- | --- | --- |
|  |  | Single Bag (24 Bars) | Single Cookie |
| Baggie Mix (g) | Cacoa powder | 84.00 | 3.50 |
|  | Moringa powder | 6.00 | 0.25 |
|  | Matcha powder | 12.00 | 0.50 |
|  | Soy Protein powder | 120.00 | 5.00 |
|  | Flaxseed powder | 12.00 | 0.50 |
|  | Cinnamon | 1.20 | 0.05 |
|  | Salt | 2.40 | 0.10 |
| Wet Ingredients (g) | Honey | 66.00 | 2.75 |
|  | Soybutter | 204.00 | 8.50 |
| Slurry (g) | Raisins | 120.00 | 5.00 |
|  | Water (ml) | 180.00 | 7.50 |
|  | Whey Protein powder | 60.00 | 2.50 |
|  | Omega 3 oil | 41.04 | 1.71 |
| Toppings (g) | Chocolate chips | 48.00 | 2.00 |
|  | Sprinkles | as needed | as needed |
| Vitamins, pure (g) | Beta Carotene | 0.013 | 0.000530 |
|  | Vitamin C | 0.08768 | 0.003654 |
|  | Vitamin D | 0.00009 | 0.000004 |
|  | Vitamin E | 0.02725 | 0.001136 |
|  | Vitamin K | 0.00022 | 0.000009 |
|  | Thiamin | 0.00197 | 0.000082 |
|  | Riboflavin | 0.00098 | 0.000041 |
|  | Niacin | 0.02997 | 0.001249 |
|  | Vitamin B6 | 0.00216 | 0.000090 |
|  | Vitamin B12 (umg)* | 0.004 | 0.000000 |
|  | Pantothenic Acid | 0.01146 | 0.000478 |
|  | Biotin | 0.00006 | 0.000003 |
|  | Choline | 1.20406 | 0.050169 |
|  | Chromium | 0.00008 | 0.000003 |
|  | Copper | 0.00234 | 0.000098 |
|  | Iodine | 0.000024 | 0.000018 |
|  | Iron | 0.0161 | 0.000794 |
|  | Manganese | 0.00331 | 0.000364 |
|  | Molybdenum | 0.0002 | 0.000005 |

TABLE 13-continued

| | | 2.9-4.15 year olds | |
| --- | --- | --- | --- |
| | | Single Bag (24 Bars) | Single Cookie |
| | Selenium | 0.00051 | 0.000005 |
| | Zinc | 0.00039 | 0.000304 |

TABLE 14

| | | 2.9-4.15 year olds | |
| --- | --- | --- | --- |
| | | Single Bag (24 Cookies) | Single Cookie |
| Vitamins, purchased form (g) | Beta Carotene | 1.272744 | 0.053031 |
| | Vitamin C | 0.0888 | 0.0037 |
| | Vitamin D | 0.033333333 | 0.001388889 |
| | Vitamin E | 0.0264 | 0.0011 |
| | Vitamin K | 0.032827701 | 0.001367821 |
| | Thiamin | 0.001974216 | 0.000082259 |
| | Riboflavin | 0.000979188 | 4.07995E−05 |
| | Niacin | 0.029967156 | 0.001248632 |
| | Vitamin B6 | 0.002156544 | 0.000089856 |
| | Vitamin B12 | 0.0004206 | 0.000017525 |
| | Pantothenic Acid | 0.012459157 | 0.000519132 |
| | Biotin | 0.00006 | 0.0000025 |
| | Choline | 3.01014 | 0.1254225 |
| | Chromium | 0.00312 | 0.00013 |
| | Copper | 0.016956522 | 0.000706522 |
| | Iodine | 0.000570674 | 2.37781E−05 |
| | Iron | 0.386384912 | 0.016099371 |
| | Manganese | 0.079404298 | 0.003308512 |
| | Molybdenum | 0.00468 | 0.000195 |
| | Selenium | 0.01218924 | 0.000507885 |
| | Zinc | 0.009341491 | 0.000389229 |

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

The invention claimed is:

1. A composition in the form of a food product for improving executive function related to undernutrition in children under four years of age, comprising:
 a) at least 20 mg of a plurality of flavonoids, wherein at least a portion of the flavonoids cross the blood-brain barrier, wherein at least one of said flavonoids is catechin or epicatechin;
 b) at least 0.5 g of omega-3 fatty acids, wherein said omega-3 fatty acids comprise EPA and DHA;
 c) at least 1 mg caffeine;
 d) a plurality of micronutrients selected from the group consisting of: iron, phosphorous, zinc, thiamine, riboflavin, niacin, vitamin B6, folate, vitamin B12, pantothenic acid, biotin, choline, chromium, copper, manganese, selenium, molybdenum, iodine, vitamin A, calcium, potassium, magnesium, vitamin E, vitamin C, a carotenoid, vitamin D, and vitamin K; and
 e) a sufficient amount of energy comprising 11-35% of calories from protein, 10-50% of calories from carbohydrates and 30-60% of calories from fat,
 wherein said food product is a capsule, a powder, a beverage, a baked good, or a raw bar.

2. The food product of claim 1, wherein said composition comprises 20-2000 mg of flavonoids.

3. The food product of claim 1, wherein said composition comprises at least 200 mg of flavonoids.

4. The food product of claim 1, wherein said composition comprises 200-500 mg of catechin and/or epicatechin.

5. The food product of claim 1, wherein said catechin and/or epicatechin are in or obtained from cocoa and/or green tea.

6. The food product claim 1, wherein said flavonoids are derived from a plant or plant component selected from the group consisting of cocoa, green tea, black tea, tea extracts, quercetin, green vegetables, spinach, moringa, matcha, kaempferol, kale, tomato, acai berry, blueberry, gingko biloba, onion, cherry tomato, cinnamon, flax seeds, chia seeds, legumes, and curcumin.

7. The food product of claim 6, wherein said composition comprises at least 50 mg of said additional flavonoids.

8. The food product of claim 1, wherein said composition comprises 100-1500 mg of EPA and/or DHA.

9. The food product of claim 1, wherein said EPA and/or DHA is in fish oil.

10. The food product of claim 1, wherein said composition comprises 1-50 mg caffeine.

11. The food product of claim 1, wherein said composition comprises cacao powder, moringa powder, matcha powder, sugar, soy protein, whey protein, fish oil, vegetable oil, peanut butter, honey, and a vitamin-mineral mix.

12. The food product of claim 1, wherein said food product comprises at least 300 kcal.

13. The composition of claim 1, wherein said executive function is working memory.

* * * * *

UNITED STATES PATENT AND TRADEMARK OFFICE
CERTIFICATE OF CORRECTION

| | | |
|---|---|---|
| PATENT NO. | : 12,161,619 B2 | Page 1 of 1 |
| APPLICATION NO. | : 17/475513 | |
| DATED | : December 10, 2024 | |
| INVENTOR(S) | : Susan Roberts, Amy Ernst and Edward Saltzman | |

It is certified that error appears in the above-identified patent and that said Letters Patent is hereby corrected as shown below:

On the Title Page

Item (71) reads:
"Applicant: TUFTS UNIVERSITY, Medford, MA (US)"

Whereas it should read:
"Applicant: TRUSTEES OF TUFTS COLLEGE, Medford, MA (US)".

Signed and Sealed this
Twenty-first Day of January, 2025

Coke Morgan Stewart
*Acting Director of the United States Patent and Trademark Office*